(12) United States Patent
Mai et al.

(10) Patent No.: US 9,784,666 B2
(45) Date of Patent: Oct. 10, 2017

(54) METHODS FOR ASSESSING CANCER CELLS USING GRANULOMETRY

(71) Applicants: Sabine Mai, Winnipeg (CA); Sjoerd Stallinga, Delfgauw (NL); Ian T. Young, Voorburg (NL); Lucas J. van Vliet, Schiedam (NL); Christiaan Righolt, Winnipeg (CA)

(72) Inventors: Sabine Mai, Winnipeg (CA); Sjoerd Stallinga, Delfgauw (NL); Ian T. Young, Voorburg (NL); Lucas J. van Vliet, Schiedam (NL); Christiaan Righolt, Winnipeg (CA)

(73) Assignee: 3D Signatures Holdings Inc., Toronto (CA)

( * ) Notice: Subject to any disclaimer, the term of this patent is extended or adjusted under 35 U.S.C. 154(b) by 5 days.

(21) Appl. No.: 14/852,143

(22) Filed: Sep. 11, 2015

(65) Prior Publication Data

US 2016/0131569 A1    May 12, 2016

Related U.S. Application Data

(60) Provisional application No. 62/049,254, filed on Sep. 11, 2014.

(51) Int. Cl.
*G06K 9/00* (2006.01)
*G01N 15/14* (2006.01)
(Continued)

(52) U.S. Cl.
CPC ..... *G01N 15/1475* (2013.01); *G06K 9/00127* (2013.01); *G06T 7/0012* (2013.01);
(Continued)

(58) Field of Classification Search
USPC ....... 382/100, 103, 106, 108, 128–134, 154, 382/162, 168, 173, 181, 199, 219, 224,
(Continued)

(56) References Cited

U.S. PATENT DOCUMENTS 7,801,682 B2 *   9/2010   Mai ........................ C12Q 1/68
                                                    382/133
8,084,203 B2 *  12/2011   Flores
                           Hernandez ........... C12Q 1/6841
                                                    435/287.2

(Continued)

OTHER PUBLICATIONS

Baddeley D, "Measurement of replication structures at the nanometer scale using super-resolution light microscopy" Nucl Acids Res 38(2): 1-11.*

(Continued)

*Primary Examiner* — Seyed Azarian
(74) *Attorney, Agent, or Firm* — Fitch, Even, Tabin & Flannery LLP

(57) ABSTRACT

A method of measuring a characteristic optionally a clinical characteristic of a cancer test cell sample comprising: characterizing nuclear organization of DNA of the test cell sample: obtaining DNA image data of the cancer test cell sample nuclei using microscopy, processing the image data using granulometry to obtain one or more data points corresponding to DNA occupied space and/or DNA low space; and quantifying a feature of the DNA occupied space and/or a feature of the DNA low space.

40 Claims, 15 Drawing Sheets

(51) Int. Cl.
  G06T 7/00    (2017.01)
  G06T 7/60    (2017.01)
  G06T 7/40    (2017.01)
  C12Q 1/68    (2006.01)
  G01N 15/10   (2006.01)

(52) U.S. Cl.
  CPC .............. *G06T 7/40* (2013.01); *G06T 7/60* (2013.01); *G01N 2015/1006* (2013.01); *G01N 2015/1488* (2013.01); *G06T 2207/10056* (2013.01); *G06T 2207/20036* (2013.01); *G06T 2207/30024* (2013.01)

(58) Field of Classification Search
  USPC ....... 382/232, 254, 274, 276, 286–291, 305, 382/312; 435/6.14, 287.2; 514/32
  See application file for complete search history.

(56) References Cited

U.S. PATENT DOCUMENTS

| | | | | |
|---|---|---|---|---|
| 8,488,863 | B2* | 7/2013 | Boucheron | G06K 9/0014 382/131 |
| 8,849,579 | B2* | 9/2014 | Mai | G01N 33/5035 435/6.14 |
| 2010/0111396 | A1* | 5/2010 | Boucheron | G06K 9/0014 382/133 |
| 2013/0178435 | A1* | 7/2013 | Mai | C12Q 1/6886 514/32 |
| 2015/0004603 | A1 | 1/2015 | Mai et al. | |
| 2015/0167058 | A1 | 6/2015 | Mai et al. | |

OTHER PUBLICATIONS

Knecht H, Righolt C, Mai S. 2013. Genomic Instability: The Driving Force behind Refractory/Relapsing Hodgkin's Lymphoma. Cancers (Basel) 5:714-25.
Knecht H, Sawan B, Lichtensztejn D, Lemieux B, Wellinger RJ, Mai S. 2009. The 3D nuclear organization of telomeres marks the transition from Hodgkin to Reed-Sternberg cells. Leukemia 23:565-73.
Korde N, Kristinsson SY, Landgren O. May 26, 2011. Monoclonal gammopathy of undetermined significance (MGUS) and smoldering multiple myeloma (SMM): novel biological insights and development of early treatment strategies. Blood 117(21):5573-5581.
Kumaran RI, Thakar R, Spector DL. 2008. Chromatin dynamics and gene positioning. Cell 132(6):929-934.
Kuppers R, Engert A, Hansmann ML. 2012. Hodgkin lymphoma. J Clin Invest 122:3439-47.
Kyle RA, Rajkumar SV. 2009. Criteria for diagnosis, staging, risk stratification and response assessment of multiple myeloma. Leukemia 23(1):3-9.
Lajoie V, Lemieux B, Sawan B, Lichtensztejn D, Lichtensztejn Z, Wellinger R, Mai S, Knecht H. Mar. 2015. LMP1 mediates multinuclearity through downregulation of shelterin proteins and formation of telomeric aggregates. Blood 125:2101-10.
Leung BO, Chou KC. 2011. Review of super-resolution fluorescence microscopy for biology. Appl Spectrosc 65(9):967-980.
Liu Y, Uttam S, Alexandrov S, Bista RK. 2014. Investigation of nanoscale structural alterations of cell nucleus as an early sign of cancer. BMC Biophys 7(1):1-16.
Luengo Hendriks CL, van Kempen GMP, van Vliet LJ. 2007. Improving the accuracy of isotropic granulometries. Pattern Recognition Letters 28:865-872.
MacLeod RA, Spitzer D, Bar-Am I, Sylvester JE, Kaufmann M, Wernich A, Drexler HG. 2000. Karyotypic dissection of Hodgkin's disease cell lines reveals ectopic subtelomeres and ribosomal DNA at sites of multiple jumping translocations and genomic amplification. Leukemia 14:1803-14.
Martin-Subero JI, Knippschild U, Harder L, Barth TF, Riemke J, Grohmann S, Gesk S, Hoppner J, Moller P, Parwaresch RM, Siebert R. 2003. Segmental chromosomal aberrations and centrosome amplifications: pathogenetic mechanisms in Hodgkin and Reed-Sternberg cells of classical Hodgkin's lymphoma? Leukemia 17:2214-9.
Nagano T, Lubling Y, Stevens TJ, Schoenfelder S, Yaffe E, Dean W, Laue ED, Tanay A, Fraser P. 2013. Single-cell Hi—C reveals cell-to-cell variability in chromosome structure. Nature 502:59-64.
Natarajan S, Juneja M, Pallam NK, Boaz K, Mohindra A, Lewis A. 2012. A novel technique to assess chromatin texture using pixel optical densitometry in oral squamous cell carcinoma. Microscopy Research and Technique 75:1119-1123.
Norrback KF, Enblad G, Erlanson M, Sundstrom C, Roos G. 1998. Telomerase activity in Hodgkin's disease. Blood 92:567-73.
Pienta KJ, Partin AW, Coffey DS. 1989. Cancer as a disease of DNA organization and dynamic cell structure. Cancer Res 49:2525-32.
Rajapakse I, Groudine M. 2011. On emerging nuclear order. J Cell Biol 192(5):711-721.
Rajkumar SV. 2005. MGUS and smoldering multiple myeloma: Update on pathogenesis, natural history, and management. Hematology Am Sac Hemalol Educ Program 1:340-345.
Rajkumar SV, Dispenzieri A, Kyle RA. 2006. Monoclonal gammopathy of undetermined significance, Waldenström macroglobulinemia, AL amyloidosis, and related plasma cell disorders: diagnosis and treatment. Mayo Clin Proc 81(5):693-703.
Righolt CH, Guffei A, Knecht H, Young IT, Stallinga S, van Vliet LJ, Mai S. 2014. Differences in nuclear DNA organization between lymphocytes, Hodgkin and Reed-Sternberg cells revealed by structured illumination microscopy. J Cell Biochem 115:1441-1448.
Sathitruangsak C, Righolt CH, Klewes L, Tammur P, Ilus T, Tamm A, Punab M, Olujohungbe A, Mai S. May 2015. Quantitative superresolution microscopy reveals differences in nuclear DNA organization of multiple myeloma and monoclonal gammopathy of undetermined significance. J Cell Biochem 116:704-10.
Schermelleh L, Carlton PM, Haase S, Shao L, Winoto L, Kner P, Burke B, Cardoso MC, Agard DA, Gustafsson MG, Leonhardt H, Sedat JW. 2008. Subdiffraction multicolor imaging of the nuclear periphery with 3D structured illumination microscopy. Science 320:1332-6.
Schermelleh L, Heintzmann R, Leonhardt H. 2010. A guide to super-resolution fluorescence microscopy. J Cell Biol 190(2):165-175.
Shroff SA, Fienup JR, Williams DR. 2009. Phase-shift estimation in sinusoidally illuminated images for lateral superresolution. J Opt Soc Am A Opt Image Sci Vis 26(2):413-424.
Solovei I, Kreysing M, LanctÔt C, Kösem S, Peichl L, Cremer T, Guck J, Joffe B. 2009. Nuclear architecture of rod photoreceptor cells adapts to vision in mammalian evolution. Cell 137(2):356-368.
Sonnen KF, Schermelleh L, Leonhardt H, Nigg EA. 2012. 3D-structured illumination microscopy provides novel insight into architecture of human centrosomes. Biol Open 1(10):965-976.
Steidl C, Diepstra A, Lee T, Chan FC, Farinha P, Tan K, Telenius A, Barclay L, Shah SP, Connors JM, van den Berg A, Gascoyne RD. 2012. Gene expression profiling of microdissected Hodgkin Reed-Sternberg cells correlates with treatment outcome in classical Hodgkin lymphoma. Blood 120:3530-40.
Szczurek AT, Prakash K, Lee HK, Zurek-Biesiada DJ, Best G, Hagmann M, Dobrucki JW, Cremer C, Birk U. 2014. Single molecule localization microscopy of the distribution of chromatin using Hoechst and DAPI fluorescent probes. Nucleus 5:331-40.
Tanabe H, Muller S, Neusser M, von Hase J, Calcagno E, Cremer M, Solovei I, Cremer C, Cremer T. 2002. Evolutionary conservation of chromosome territory arrangements in cell nuclei from higher primates. Proc Natl Acad Sci U S A 99:4424-9.
Turnbull L, Strauss MP, Liew AT, Monahan LG, Whitchurch CB, Harry EJ. 2014. Super-resolution imaging of the cytokinetic Z ring in live bacteria using fast 3D-structured illumination microscopy (f3D-SIM). J Vis Exp 29(91):1-13.
Verbeek PW, van Vliet LJ. 1993. Estimators of 2D edge length and position, 3D surface area and position in sampled grey-valued images. Bioimaging 1:47-61.
Wang Y, Maharana S, Wang MD, Shivashankar GV. 2014. Super-resolution microscopy reveals decondensed chromatin structure at transcription sites. Sci Rep 4:4477.

(56) References Cited

OTHER PUBLICATIONS

Wicker K, Mandula O, Best G, Fiolka R, Heintzmann R. 2013. Phase optimisation for structured illumination microscopy. Opt Express 21(2):2032-2049.

Young IT. 1977. Proof without prejudice: use of the Kolmogorov-Smirnov test for the analysis of histograms from flow systems and other sources. J Histochem Cytochem 25:935-41.

Young IT, Verbeek PW, Mayall BH. 1986. Characterization of chromatin distribution in cell nuclei. Cytometry 7:467-474.

Zingone A, Kuehl WM. 2011. Pathogenesis of monoclonal gammopathy of undetermined significance (MGUS) and progression to multiple myeloma. Semin Hematol 48(1):4-12.

Young, Ian T., et al. Characterization of Chromatin Distribution in Cell Nuclei. 1986, Cytometry 7:467-474.

Righolt, Christiaan H. et al. Differences in Nuclear DNA Organization Between Lymphocytes, Hodgkin and Reed-Sternberg Cells Revealed by Structured Illumination Microscopy. Journal of Cellular Biochemistry. 2014, 115:1441-1448.

Lansdorp, Peter M., et al. Heterogeneity in Telomere Length of Human Chromosomes. 1996 Oxford University Press. 1996, vol. 5, No. 5: 685-691.

Adebayo Awe J, Xu MC, Wechsler J, Benali-Furet N, Cayre YE, Saranchuk J, Drachenberg D, Mai S. Feb. 2013. Three-Dimensional Telomeric Analysis of Isolated Circulating Tumor Cells (CTCs) Defines CTC Subpopulations. Transl Oncol vol. 6, No. 1, pp. 51-65.

Baddeley D, Chagin VO, Schermelleh L. 2010. Measurement of replication structures at the nanometer scale using super-resolution light microscopy. Nucl Acids Res 38(2):1-11.

Bins M, Landeweerd GH, Gelsema ES, van Montfort LH, Halie MR. 1981. Texture of white blood cells expressed by the counting densitogram. Cytometry 1:321-324.

Boulon S, Westman BJ, Hutten S, Boisvert FM, Lamond AI. 2010. The nucleolus under stress. Mol Cell 40:216-27.

Knecht H, Kongruttanachok N, Sawan B, Brossard J, Prevost S, Turcotte E, Lichtensztejn Z, Lichtensztejn D, Mai S. Aug. 2012. Three-dimensional Telomere Signatures of Hodgkin- and Reed-Sternberg Cells at Diagnosis Identify Patients with Poor Response to Conventional Chemotherapy. Transl Oncol vol. 5, No. 4, pp. 269-277.

Branco MR, Pombo A. 2006. Intermingling of chromosome territories in interphase suggests role in translocations and transcription-dependent associations. PLoS Biol 4:e138.

Brousset P, al Saati T, Chaouche N, Zenou RC, Schlaifer D, Chittal S, Delsol G. Jan. 1, 1997. Telomerase activity in reactive and neoplastic lymphoid tissues: infrequent detection of activity in Hodgkin's disease. Blood vol. 89, No. 1, pp. 26-31.

Carlton PM. 2008. Three-dimensional structured illumination microscopy and its application to chromosome structure. Chromosome Res 16(3):351-365.

Cogger VC, McNerney GP, Nyunt T, DeLeve LD, McCourt P, Smedsrød B, Le Couteur DG, Huser TR. 2010. Three-dimensional structured illumination microscopy of liver sinusoidal endothelial cell fenestrations. J Struct Biol 171(3):382-388.

Cremer T, Cremer C. 2006a. Rise, fall and resurrection of chromosome territories: a historical perspective. Part I. The rise of chromosome territories. Eur J Histochem 50:161-76.

Cremer T, Cremer C. 2006b. Rise, fall and resurrection of chromosome territories: a historical perspective. Part II. Fall and resurrection of chromosome territories during the 1950s to 1980s. Part III. Chromosome territories and the functional nuclear architecture: experiments and models from the 1990s to the present. Eur J Histochem 50:223-72.

Cremer T, Cremer C. 2010. Chromosome territories. Cold Spring Harb Perspect Biol 2(3):1-22.

Dimopoulos MA, Terpos E. 2010. Multiple myeloma. Ann Oncol 21(7):vii143-vii 150.

Duin RPW, Juszczak P, Paclik P, Pekalska E, de Ridder D, Tax DMJ, Verzakov S. 2007. PRTools, A Matlab toolbox for pattern recognition. Delft, The Netherlands: Delft University of Technology.

Fong KW, Li Y, Wang W, Ma W, Li K, Qi RZ, Liu D, Songyang Z, Chen J. 2013. Whole-genome screening identifies proteins localized to distinct nuclear bodies. J Cell Biol 203:149-64.

Frohn JT, Knapp HF, Stemmer A. 2000. True optical resolution beyond the Rayleigh limit achieved by standing wave illumination. Proc Natl Acad Sci U S A 97:7232-6.

Green LC, Kalitsis P, Chang TM, Cipetic M, Kim JH, Marshall O, Turnbull L, Whitchurch CB, Vagnarelli P, Samejima K, Earnshaw WC, Chao KHA, Hudson DF. 2011. Contrasting roles of condensin I and condensin II in mitotic chromosome formation. J Cell Sci 125(6):1591-1604.

Guffei A, Sarkar R, Klewes L, Righolt C, Knecht H, Mai S. 2010. Dynamic chromosomal rearrangements in Hodgkin's lymphoma are due to ongoing three-dimensional nuclear remodeling and breakage-bridge-fusion cycles. Haematologica 95:2038-46.

Gustafsson MG. 2000. Surpassing the lateral resolution limit by a factor of two using structured illumination microscopy. J Microsc 198:82-7.

Gustafsson MG, Shao L, Carlton PM, Wang CJ, Golubovskaya IN, Cande WZ, Agard DA, Sedat JW. 2008. Three-Dimensional Resolution Doubling in Wide-Field Fluorescence Microscopy by Structured Illumination. Biophys J 94(12):4957-4970.

Heintzmann R, Cremer CG. 1999. Laterally modulated excitation microscopy: improvement of resolution by using a diffraction grating, p. 185-196.

Hell SW. 2007. Far-field optical nanoscopy. Science 316:1153-1158.

Hsu SM, Zhao X, Chakraborty S, Liu YF, Whang-Peng J, Lok MS, Fukuhara S. May 1988. Reed-Sternberg cells in Hodgkin's cell lines HDLM, L-428, and KM-H2 are not actively replicating: lack of bromodeoxyuridine uptake by multinuclear cells in culture. Blood 71:1382-9.

Johnson NA, Savage KJ, Ludkovski O, Ben-Neriah S, Woods R, Steidl C, Dyer MJ, Siebert R, Kuruvilla J, Klasa R, Connors JM, Gascoyne RD, Horsman DE. 2009. Lymphomas with concurrent BCL2 and MYC translocations: the critical factors associated with survival. Blood 114:2273-9.

Jones RJ, Gocke CD, Kasamon YL, Miller CB, Perkins B, Barber JP, Vala MS, Gerber JM, Gellert LL, Siedner M, Lemas MV, Brennan S, Ambinder RF, Matsui W. 2009. Circulating clonotypic B cells in classic Hodgkin lymphoma. Blood 113:5920-6.

Kanakry JA, Li H, Gellert LL, Lemas MV, Hsieh WS, Hong F, Tan KL, Gascoyne RD, Gordon LI, Fisher RI, Bartlett NL, Stiff P, Cheson BD, Advani R, Miller TP, Kahl BS, Horning SJ, Ambinder RF. 2013. Plasma Epstein-Barr virus DNA predicts outcome in advanced Hodgkin lymphoma: correlative analysis from a large North American cooperative group trial. Blood 121:3547-53.

Klewes L, Vallente R, Dupas E, Brand C, Grün D, Guffei A, Sathitruangsak C, Awe JA, Kuzyk A, Lichtensztejn D, Tammur P, Ilus T, Tamm A, Punab M, Rubinger M, Olujohungbe A, Mai S. Dec. 2013. Three-dimensional nuclear telomere organization in multiple myeloma. Transl Oncol vol. 6, No. 6 pp. 749-756.

Knecht et al. 3D nuclear organization of telomeres in the Hodgkin cell lines U-HO1 and U-HO1-PTPN1: PTPN1 expression prevents the formation of very short telomeres including "t-stumps". BMC Cell Biology, 2010, vol. 11, No. 99, pp. 1-10.

* cited by examiner

METHODS FOR ASSESSING CANCER CELLS USING GRANULOMETRY

CROSS REFERENCE TO RELATED APPLICATION

This is a United States patent application which claims the benefit of 35 U.S.C. §119 based on the priority of U.S. Provisional Patent Application No. 62/049,254, filed Sep. 11, 2014, which is incorporated herein by reference in its entirety.

FIELD

The disclosure pertains to methods for assessing cancer cells for example Hodgkin's lymphoma and multiple myeloma cells.

BACKGROUND

The nuclear architecture and its cancer-related changes have been studied since Boveri first postulated that the nuclear architecture differs between normal and cancer cells [Boveri, 1914; Boveri, 2008]. Over the course of the last century the structure of DNA has been unraveled at various length scales. The structure by itself does not, however, reveal its spatial organization within the nucleus. Many current models about the nuclear architecture are studied in animals and human cell lines. For clinical applications such models also need to be validated in primary human tumor cells.

Chromosomes occupy distinct regions in the interphase nucleus, designated as chromosome territories (CTs) [Cremer and Cremer, 2006a; Cremer and Cremer, 2006b]. The position of each human CT inside the nucleus is determined by its size and gene density [Tanabe et al., 2002]. As the spatial distribution of DNA is non-random, it is important to assess the spatial DNA structure. This would include measurements at length scales larger than the typical sizes of the quaternary nucleic acid structure.

Microscopic analyses of the DNA structure in cell nuclei have been performed since the wide-scale availability of digital image processing. Automatic estimation of the number of low and high density DNA regions within a white blood cell has been performed since the 1980s [Bins et al., 1981].

It has also been noted that chromatin is structurally organized on various length scales that can be made visible using light microscopy [Einstein et al., 1998]. Differences in the microscopic DNA structure have been described using various names, including chromatin condensation, chromatin structure and chromosome packaging, in a variety of diseases, including cancer [Hannen et al., 1998; Natarajan et al., 2012; Vergani et al., 1999].

3D structured illumination microscopy (3D-SIM) is a superresolution imaging modality that has only recently found its way to the biology laboratory. This methodology offers a higher image resolution than conventional epifluorescence widefield microscopy through the use of heterodyne detection of a fluorescent sample illuminated by a periodic pattern [Cragg and So, 2000; Frohn et al., 2000; Gustafsson, 2000; Heintzmann and Cremer, 1999]. 3D-SIM images of DNA, stained with DAPI, reveal nuclear pore protein complex features that had not been seen with conventional microscopy methods [Schermelleh et al., 2008]. Investigation of the nuclear architecture using FISH (fluorescent in situ hybridization) showed that, during FISH experiments, key characteristics of the ultrastructure are preserved [Markaki et al., 2012].

SUMMARY

An aspect includes a method of measuring a characteristic optionally a clinical characteristic of a cancer test cell sample comprising:
  a. characterizing nuclear organization of DNA of the test cell sample comprising:
    i. obtaining DNA image data of the cancer test cell sample nuclei using microscopy;
    ii. processing the image data using granulometry to obtain one or more data points corresponding to DNA occupied space and/or DNA low space; and
  b. quantifying a feature of the DNA occupied space and/or a feature of the DNA low space.

Another aspect includes a method of assessing a characteristic optionally a clinical characteristic of a cancer test cell sample comprising:
  a. characterizing nuclear organization of DNA of the test cell sample:
    i. obtaining DNA image data of the cancer test cell sample nuclei;
    ii. processing the image data using granulometry to obtain one or more data points corresponding to DNA occupied space and/or DNA low space;
  b. quantifying a feature of the DNA occupied space and/or a feature of the DNA low space;
  c. comparing the quantified feature(s) for the DNA occupied space and/or DNA low space to another cancer sample, a control sample or threshold;
  d. identifying an increase or decrease in the quantified feature compared to the control;
  wherein an increase or a decrease in the quantified feature compared to the control is indicative of the characteristic optionally the clinical characteristic of the cancer test sample.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

contains a tri-directional anaphase bridge between several of the subnuclei (dashed circle in Diii). The intensities of all images are linearly stretched between their minimum and maximum value. Note that the nuclear organization of the DNA becomes visible by comparing the SIM images to the widefield images. Also note the difference in the structure between the different images.

Figure 1:
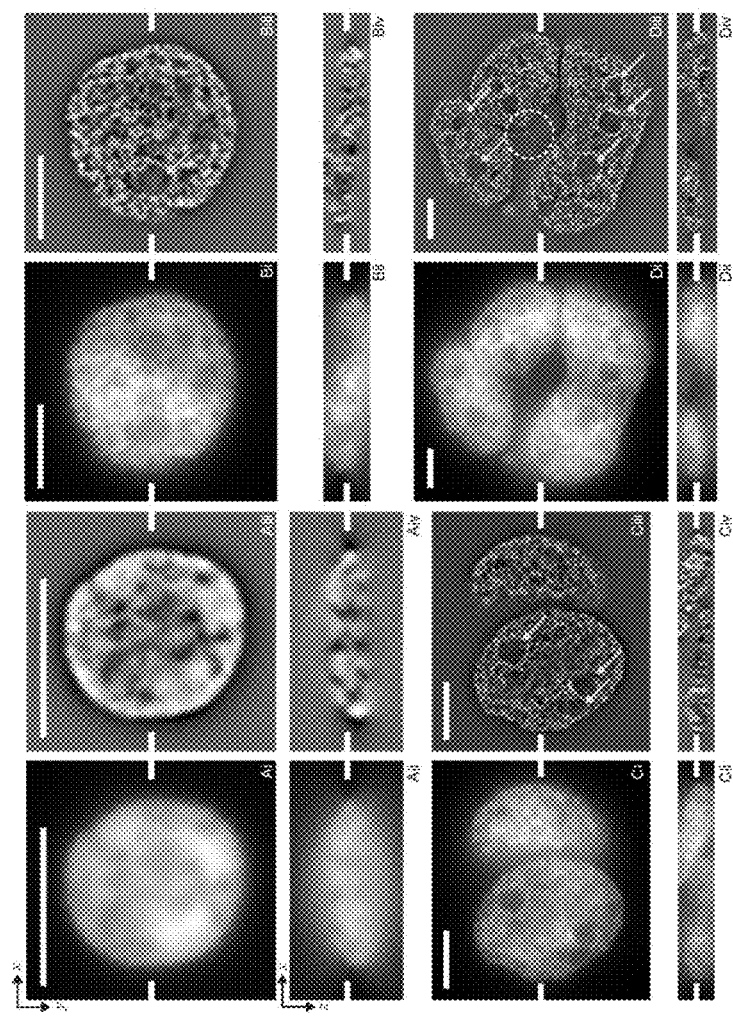
FIG. 1: Slices from DAPI stained cell nuclei of a control lymphocyte (A), a Hodgkin cell (B), a binucleated Reed-Sternberg cell (C), and a multinucleated Reed-Sternberg cell (D). Widefield images are shown in images (i,ii) and unclipped SIM images in (iii,iv). The top row (i,iii) shows a lateral (x,y)-slice and the bottom row (ii,iv) an axial (x,z)-slice. The scale bars are 5 µm in each lateral slice—note the increasing size from A to D—the tick marks in the middle of each panel indicate the positions of the corresponding orthogonal planes. The arrows denote "holes" in the DNA distribution of these cells. Note that not all apparent holes are indicated to maintain clarity. The multinucleated cell (D)
Figure 2:
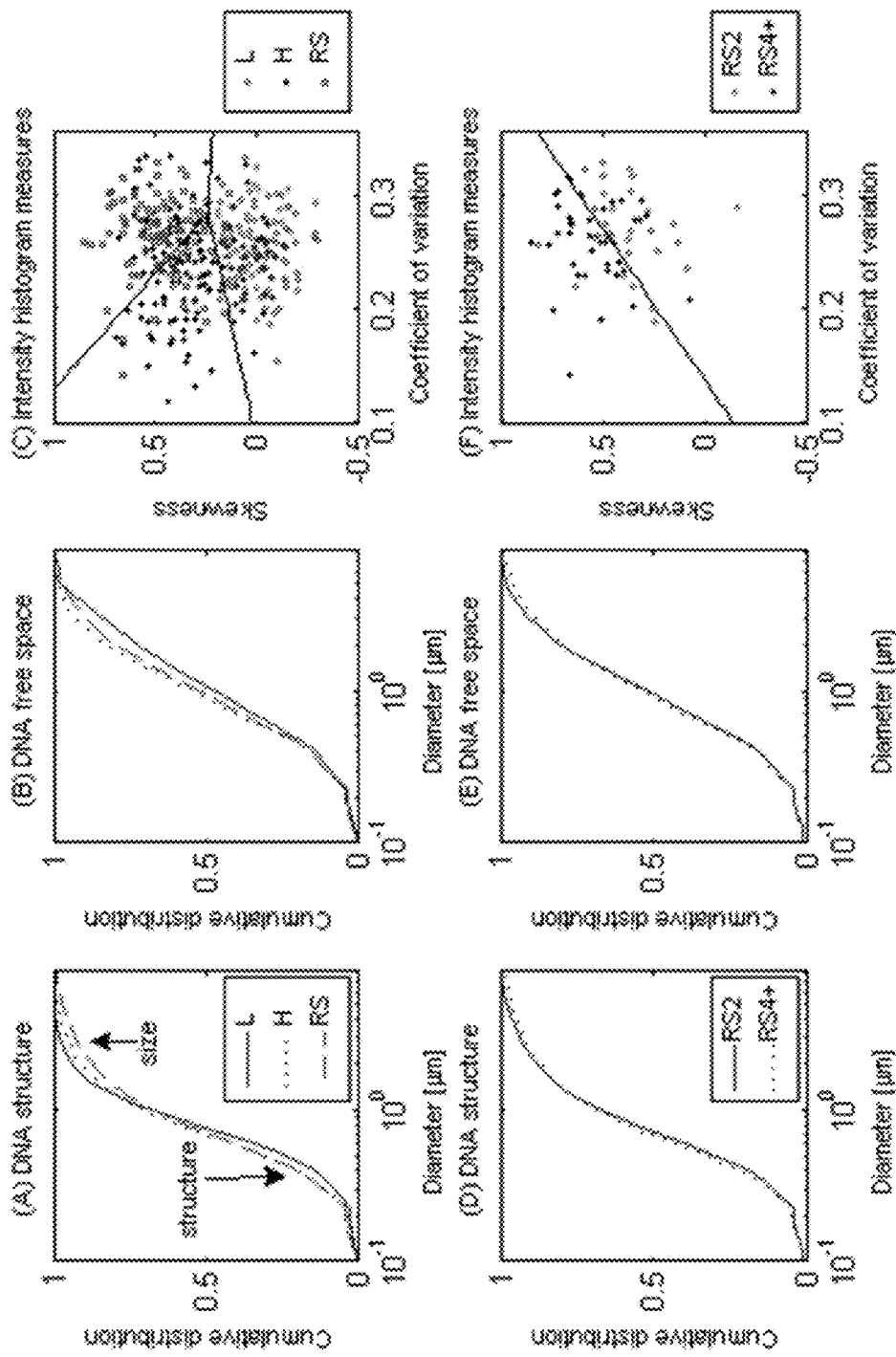

FIG. 2: Measurements on SIM images of DAPI-stained nuclei of the size distribution of the DNA structure (DNA occupied space) and DNA-free space, as well as the intensity histogram. These visible structures are depicted in FIG. 1. The top row (A-C) shows these measures for lymphocytes (L, solid lines and circles), Hodgkin cells (H, dotted lines and crosses) and Reed-Sternberg cells (RS, dash lines and squares). The bottom row (D-F) illustrates binucleated RS cells (RS, solid lines and circles) and RS cells with 4 or more subnuclei (RS4+, dotted lines and crosses). (A,D) Show the cumulative distribution function (CDF) of the size of the of the DNA occupied space, (B,E) the cumulative distribution function (CDF) of the size of the DNA-poor space. All these size distributions are measured with a granulometry. The difference in the sub-micron size range is caused by differences in the DNA structure size. Differences in size in the order of several μm are due to the difference in cell size. Both regimes are indicated with an arrow in the top left plot. (C,F) Show the coefficient of variation and skewness of the intensity histogram of these cells. The black lines are the Fisher linear discriminants. See FIG. 7 for measurements on the widefield images of the same cells. All differences between the granulometries are significant at the 5% significance level, except RS2 vs. RS4+ for the DNA free space.

Figure 3:
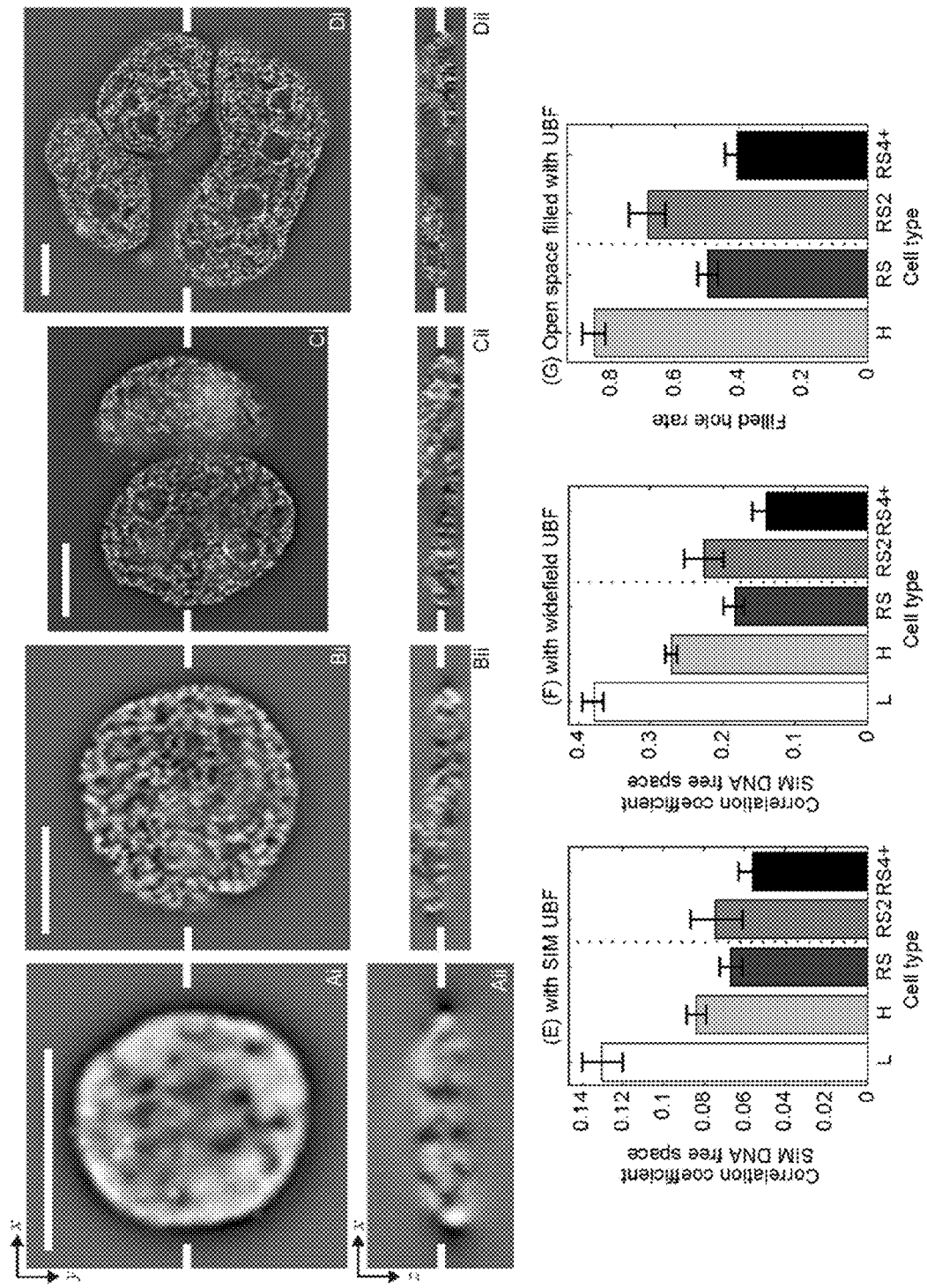

FIG. 3: DAPI SIM image in greyscale and UBF widefield image in greyscale for the same cells as FIG. 1 with a lymphocyte (A), an H cell (B), a binucleated RS cell (C), and a multinucleated RS cell (D). The top row (i) shows a lateral (x,y)-slice and the bottom row (ii) a (x,z)-slice from the same cell. The scale bars are 5 μm in each lateral slice. The tick marks in the middle of each panel indicate the positions of the corresponding orthogonal planes. The DAPI signal intensities are linearly stretched between the minimum and maximum value, the widefield UBF signal intensities are linearly scaled between the 5th and 100th percentile over the nucleus. Values below the $5^{th}$ percentile were clipped. Note that clusters of UBF, a transcription factory, are located in DNA-free space, including some of the holes identified by arrows in FIG. 1. Not all holes contain UBF, as is most apparent in panels (D). The bottom row (E-G) shows measurements relating to the spatial UBF distribution with regard to the nucleus for the five groups of cells. The bars indicate the sample mean and the error bars the standard error of the mean. The bottom left (E) indicates the correlation coefficient between the DNA-free space SIM image and SIM UBF image. The bottom middle (F) displays the correlation coefficient between the DNA-free space SIM image and widefield UBF image. The bottom right (G) indicates the manually counted fill rate for the "holes" in the DNA structure (arrows in FIG. 1). Because there are no clearly visible holes in the lymphocytes, the H and RS numbers are only shown. All differences in correlation coefficients and filled-hole-rates on either side of the dashed lines are significant at the 5% level, except RS2 vs. RS4+ in panel (E).

Figure 4:
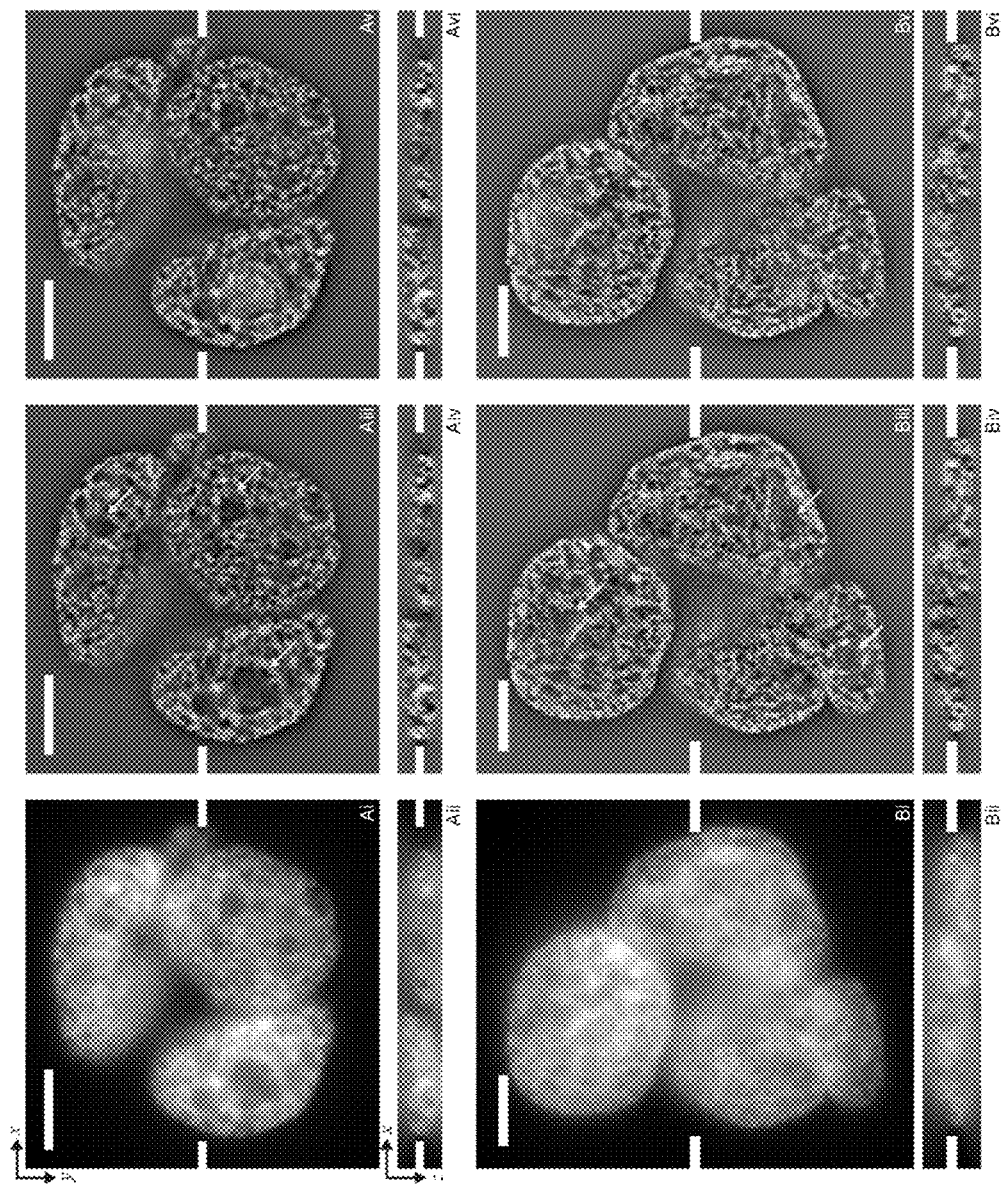

FIG. 4: Slices from a trinucleated Reed-Sternberg cell (A) and a tetranucleated Reed-Sternberg cell (B). Widefield images of the DAPI signal are shown in images (i,ii), unclipped SIM DAPI images in (iii,iv) and grayscale DAPI SIM images with the widefield UBF images superimposed are shown in (v,vi). The top and third rows (i,iii,v) shows a lateral (x,y)-slice and the second and bottom rows (ii,iv,vi) an axial (x,z)-slice from the same cell. The scale bars are 5 μm in each lateral slice. The tick marks in the middle of each panel indicate the positions of the corresponding orthogonal planes. The DAPI signal intensities of the SIM images are linearly stretched between the minimum and maximum value, the widefield UBF signal intensities are linearly scaled between the 5th and 100th percentile over the nucleus. Values below the $5^{th}$ percentile were clipped. The arrows denote "holes" in the DNA distribution of these cells. Note that not all apparent holes are indicated.

Figure 5:
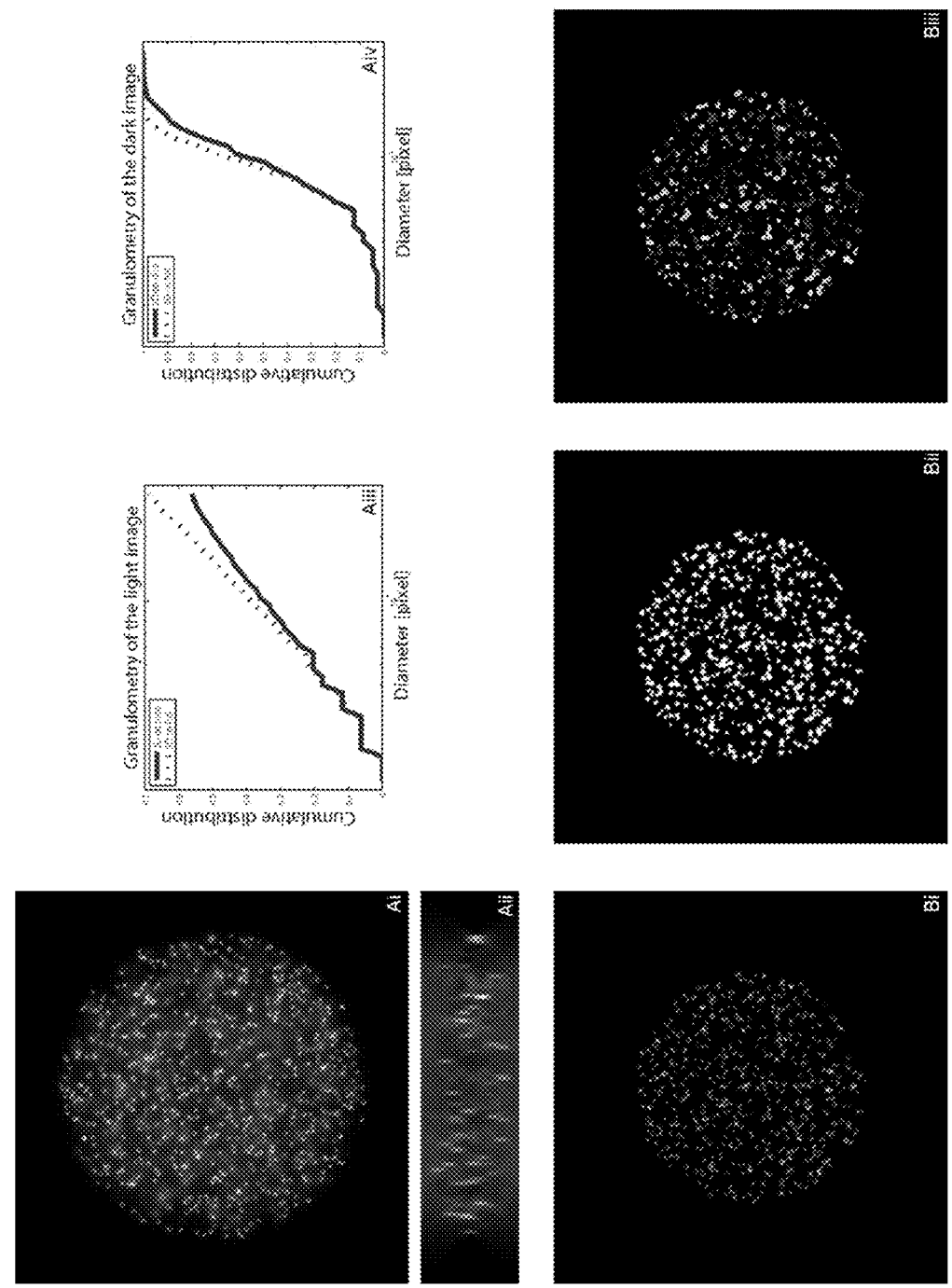

FIG. 5: Several images illustrating the granulometry tests. A 3D image (A) was created for which the central z-slice (which is taken as the 2D input) is shown in (Ai), an axial (x,z)-slice in shown in (Aii). The granulometries for both the full 3D image (dashed lines) and the selected 2D slice (solid lines) are shown for the light objects in (Aiii) and the dark objects in (Aiv). Note that the granulometry of the dark image is not the complement of the granulometry of the light image. The tests for the estimation of N are illustrated in (B). One of a thousand created 2D slices is depicted in (Bi), its corresponding input for the granulometry in (Bii) and the labeled version of a segmented version in (Biii). The intensity of all greyscale images are linearly stretched between the minimum and maximum value over the image.

Figure 6:
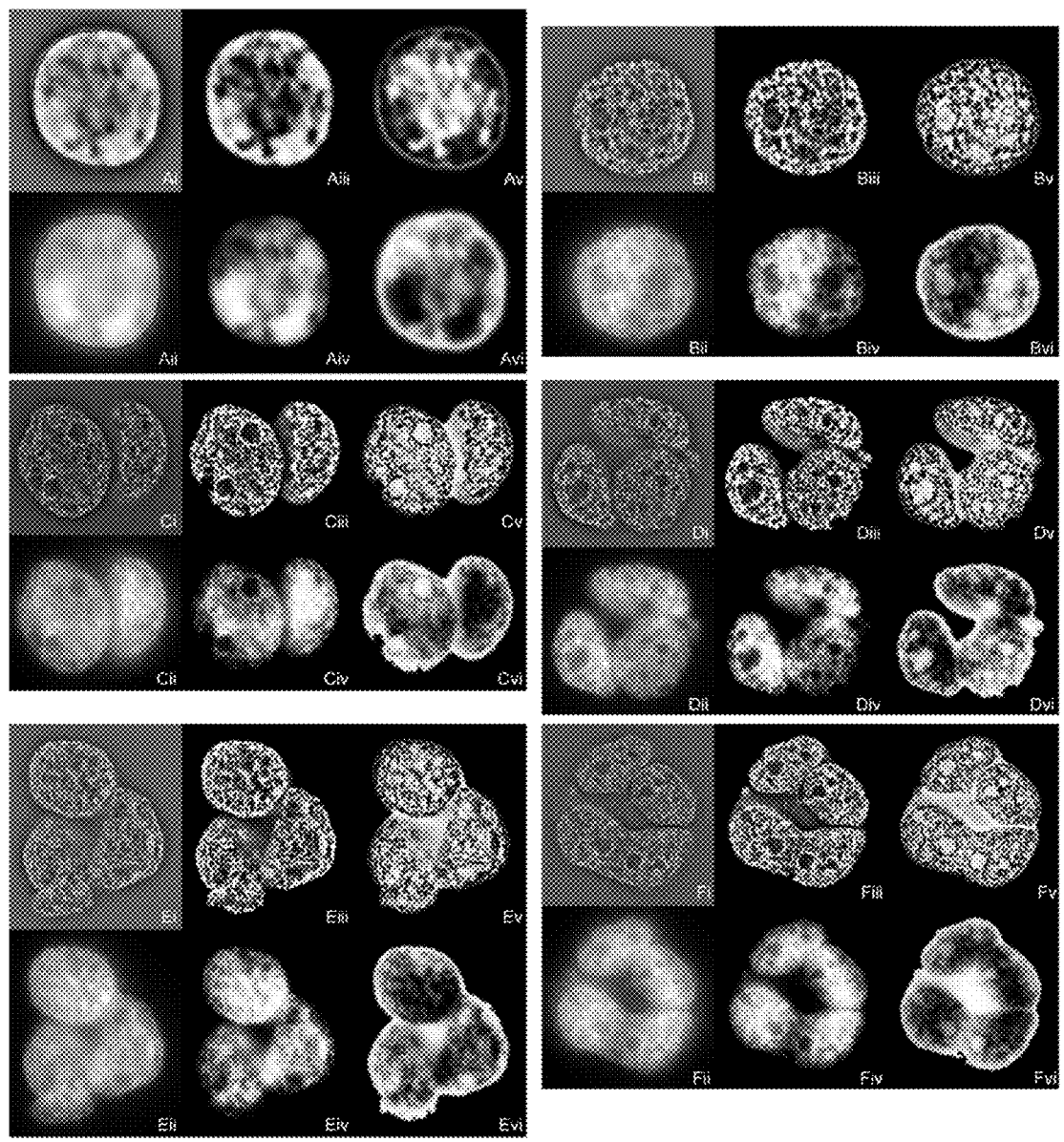

FIG. 6: Granulometry input images for a lymphocyte (A), an H cell (B), a binucleated RS cell (C), a trinucleated RS cell (D), a tetranucleated RS cell (E), and a multinucleated RS cell (F). The top row (i,iii,v) of each group of six shows the SIM image, the bottom row (ii,iv,vi) the widefield image. The cell images have different scales, see FIGS. 1 and 4 for scales. The left columns (i,ii) show the original DAPI images in grey scale with the outline of the nuclear mask, the result of the isodata threshold, in black. The middle columns (iii,iv) depict the input for the DNA structure granulometry after erf-clipping. The right columns (v,vi) show the input for the DNA-free space granulometry, which is the negative of the erf-clipped DNA image inside the nucleus.

Figure 7:
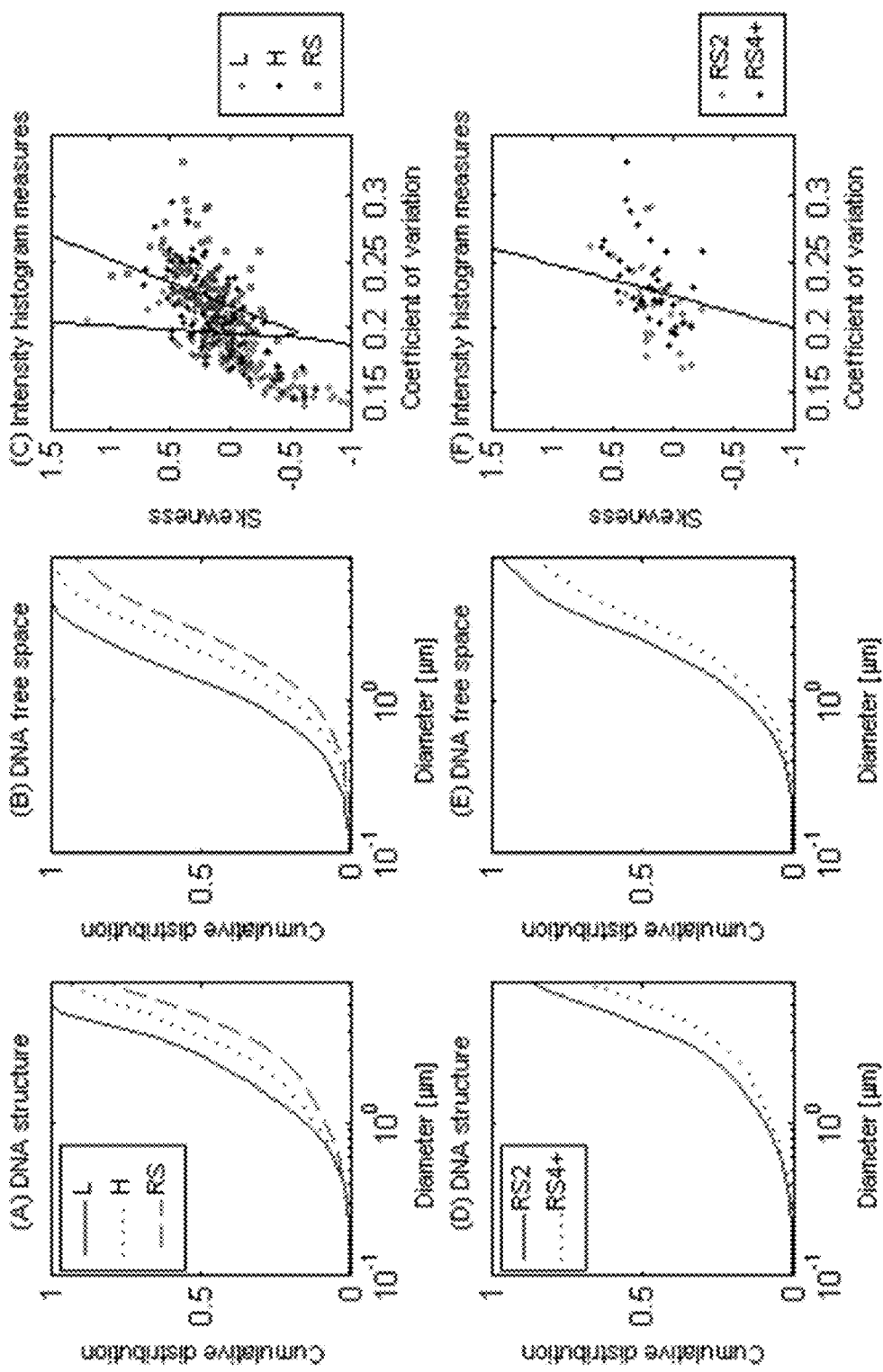

FIG. 7: Granulometries and histogram-based cell properties measured from widefield images. The top row compares lymphocytes (L, solid lines and circles), Hodgkin cells (H, dotted lines and crosses) and Reed-Sternberg cells (RS, dashed lines and squares). The bottom row illustrates binucleated RS cells (RS, solid lines and circles) and RS cells with 4 or more subnuclei (RS4+, dotted lines and crosses). The left column shows the cumulative size distribution of the DNA structure (A,D), the middle column the cumulative size distribution of the DNA free space (B,E). All these size distributions are measured with a granulometry. The right column shows the coefficient of variation and skewness of the intensity histogram of these cells (C,F). The black lines are the discrimination functions derived from Fisher linear discriminant analysis. See FIG. 2 for the same measurements for the SIM images.

Figure 8:
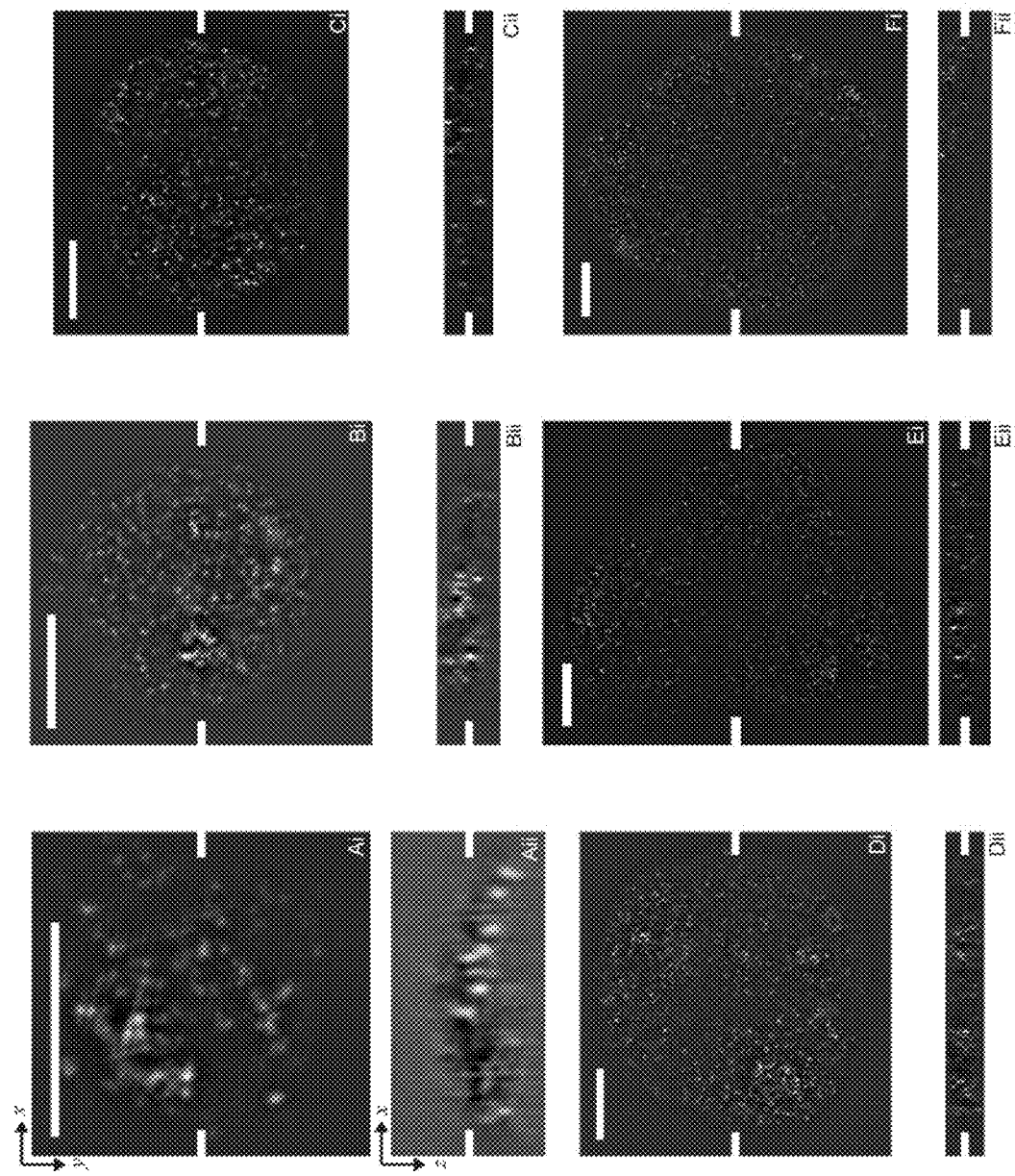

FIG. 8: SIM image of the UBF channel for a lymphocyte (A), an H cell (B), a binucleated RS cell (C), a trinucleated RS cell (D), a tetranucleated RS cell (E), and a multinucleated RS cell (F). Lateral (x,y) slices are shown in (i), axial (x,z) slices in (ii). The scale bars are 5 μm in each lateral slice. The tick marks in the middle of each panel indicate the positions of the corresponding orthogonal planes. The image intensities are linearly stretched between the minimum and maximum value for each slice. A few SIM-related image artifacts are clearly visible.

Figure 9:
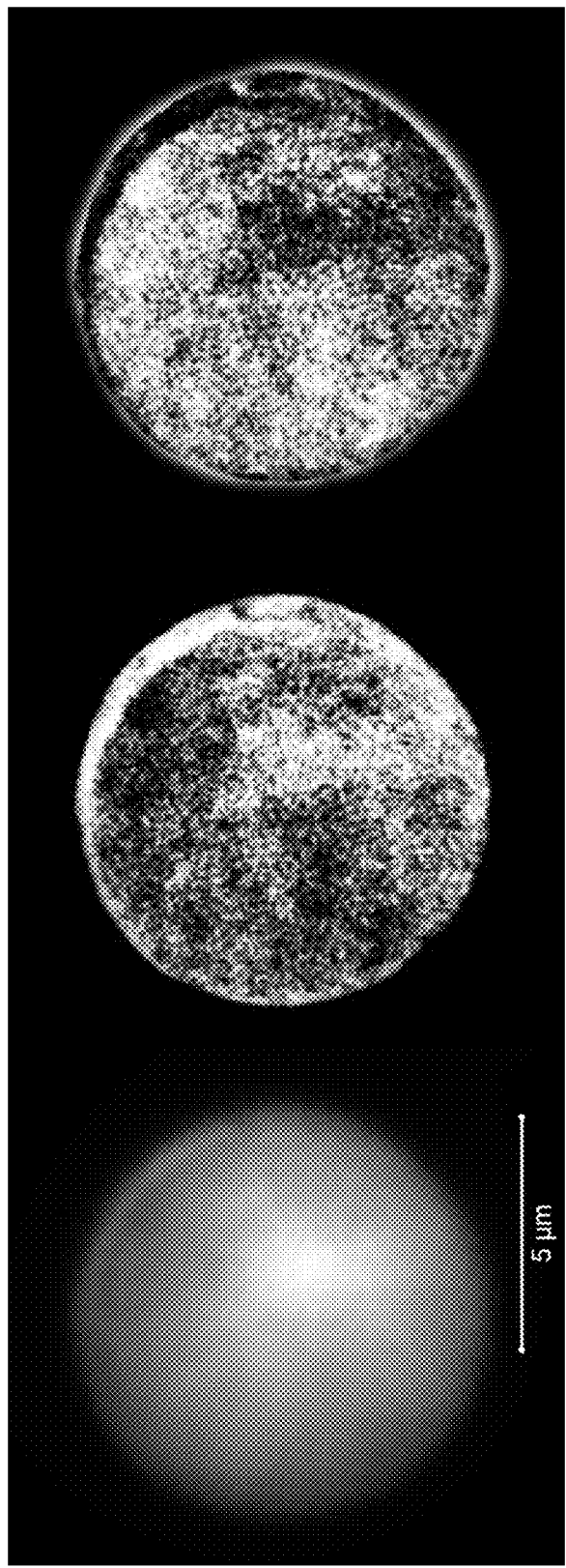

FIG. 9: A widefield image and SIM images of lymphocytes.

Figure 10:
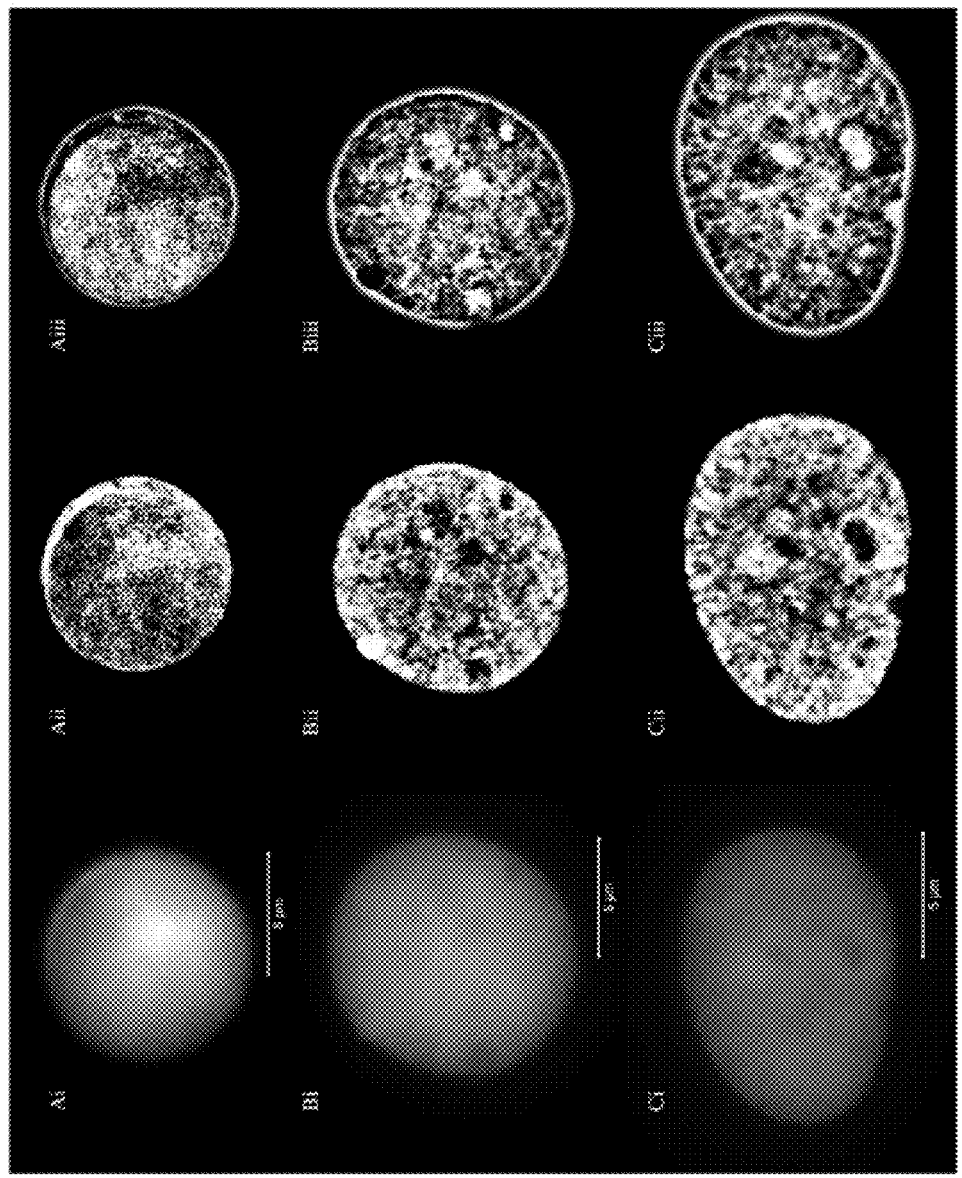

FIG. 10: Representative images from DAPI-stained nuclei of a normal lymphocyte (A), MGUS nucleus (B) and MM nucleus (C). Widefield images are shown in images (i), unclipped SIM images in images (ii), and negative unclipped SIM images in images (iii). The scale bars are 5 µm in length. The SIM images showed the DNA structures in greater detail compared to the widefield images. Note the difference in the DNA structures and also the size of the nuclei between the different cell types. Quantitative Super-resolution Microscopy Reveals Differences in Nuclear DNA Organization of Multiple Myeloma and Monoclonal Gammopathy of Undetermined Significance.

Figure 11:
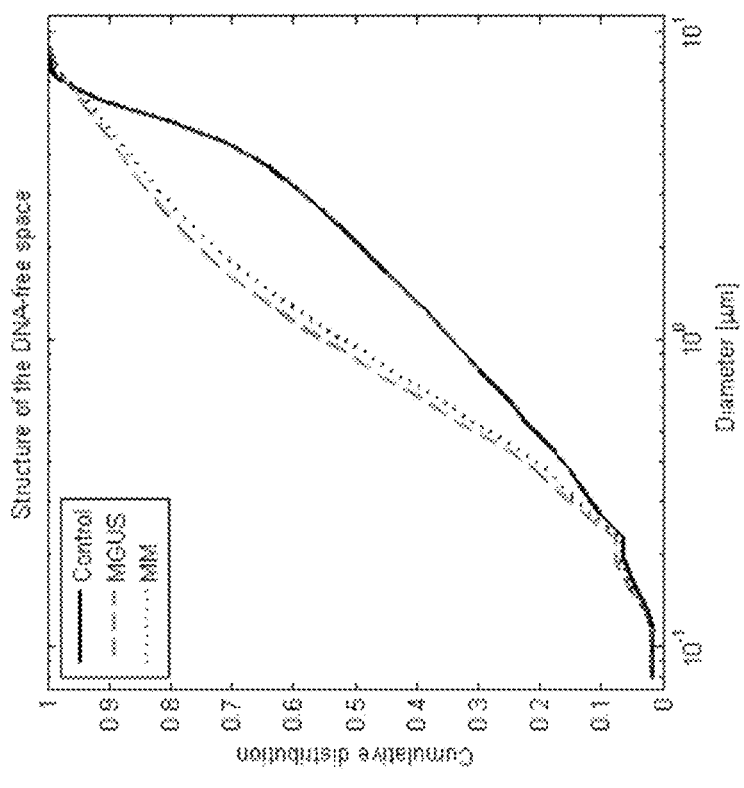
Figure 11:
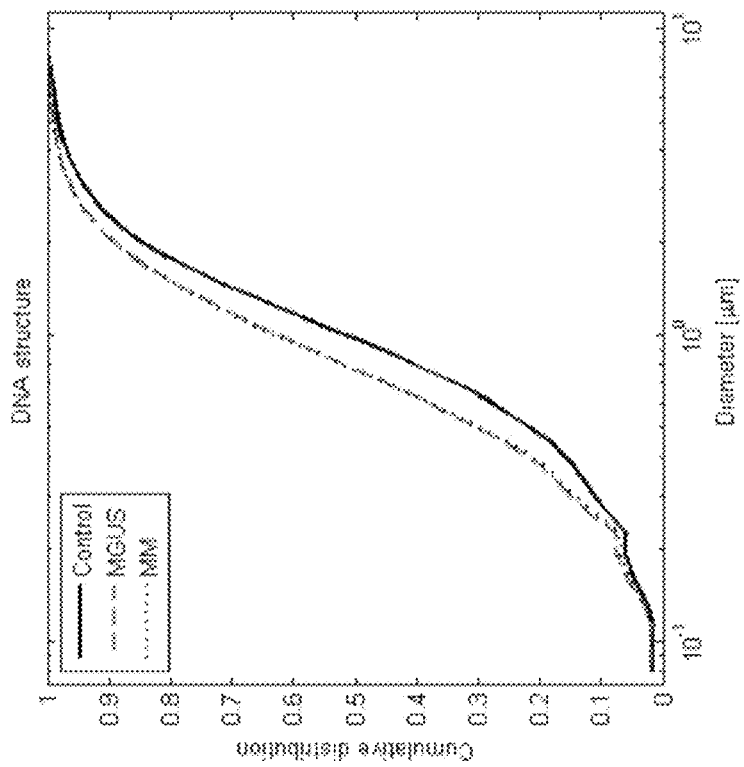

FIG. 11: Measurement of the size distribution of the DNA structure of normal lymphocyte (solid lines), MGUS (dashed lines) and MM (dotted lines) using granulometry. While the differences in nucleus size of each cell type might reach up to several µm, the differences in the DNA structure size were represented in the sub-micron size range. Granulometries revealed a significant increase in the amount of DNA submicron structure in MGUS and MM nuclei compared to control lymphocyte ($P=10^{-88}$) (A). The differences between MGUS and MM are significant for DNA-free space ($P=10^{-8}$) but not for DNA submicron structure ($P=0.68$) (B). Note that both MGUS and MM nuclei were significantly larger in size than normal lymphocytes.

Figure 12:
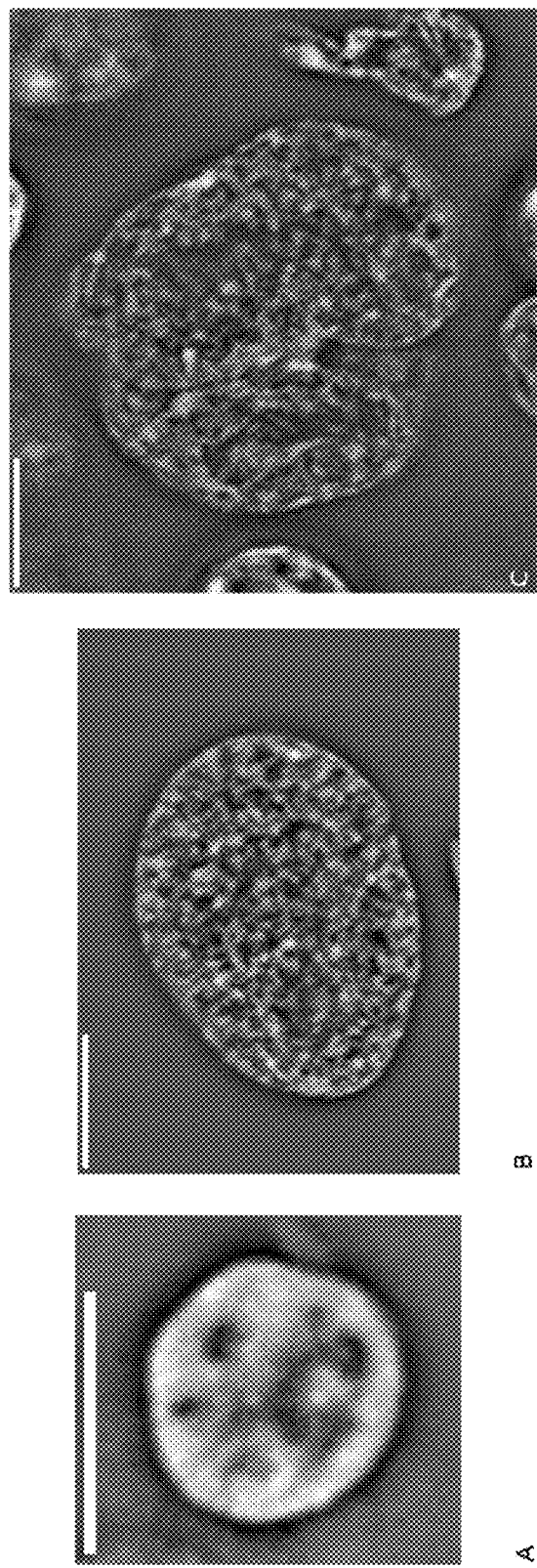

FIG. 12: Structured illumination images of DAPI-stained cell nuclei of a lymphocyte (A), a Hodgkin cell (B) and a Reed-Sternberg cell (C) from a diagnostic lymph node biopsy of a patient entering long lasting remission. Slide preparation and imaging was performed as described herein. A full 3D SIM image was recorded and reconstructed; analysis was done on the single (x,y)-slices depicted. Note the differences in both the DNA structure and the structure of the DNA-free space. The scale bars are 5 µm for each image.

Figure 13:
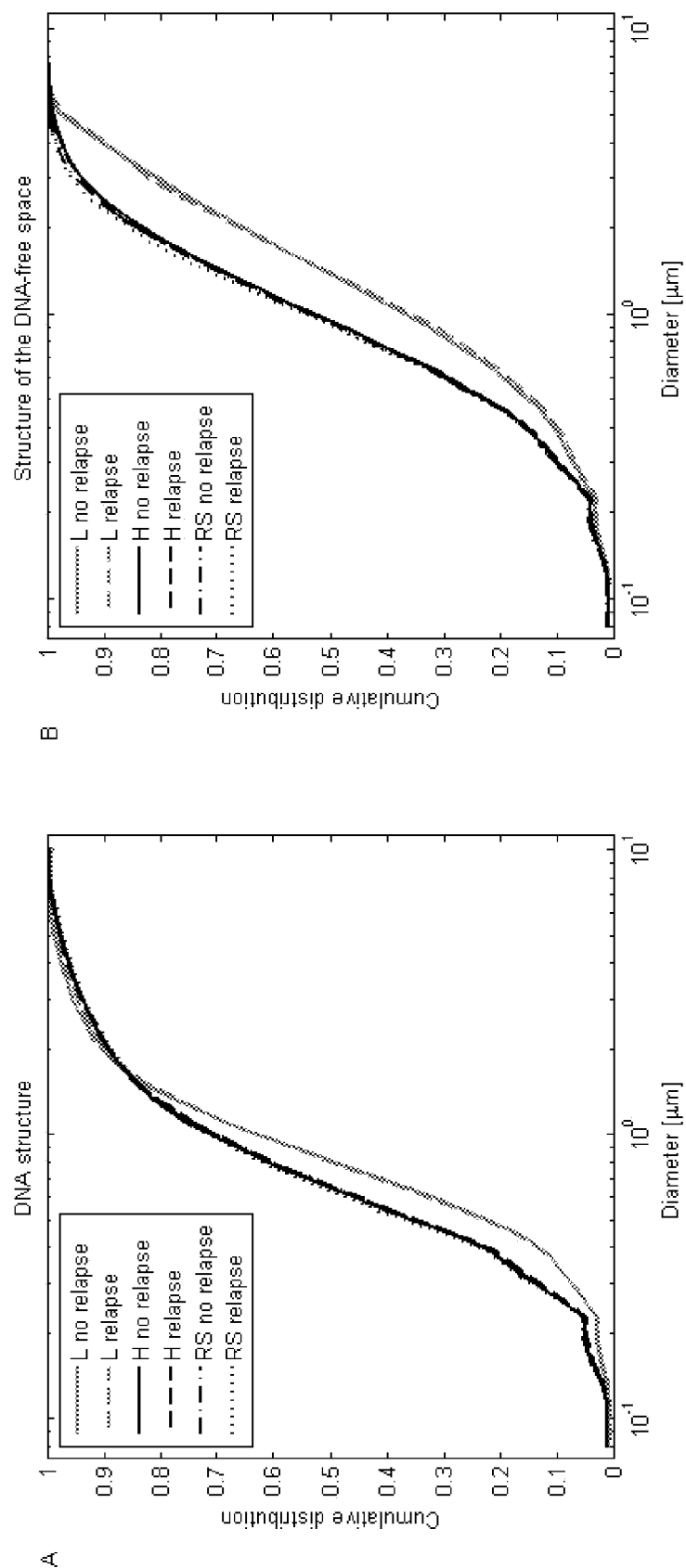

FIG. 13: Measurements on SIM images of DAPI-stained cell nuclei. The cumulative size distribution is measured using granulometries for both the DNA structure (A) and the structure of the DNA-free space (B). The measurements are shown for lymphocytes (L, grey solid and dashed lines), Hodgkin cells (H, black solid and dashed lines) and Reed-Sternberg cells (RS, black dash-dotted and dotted lines) for both non-relapsed patients and relapsed patients.

Figure 14:
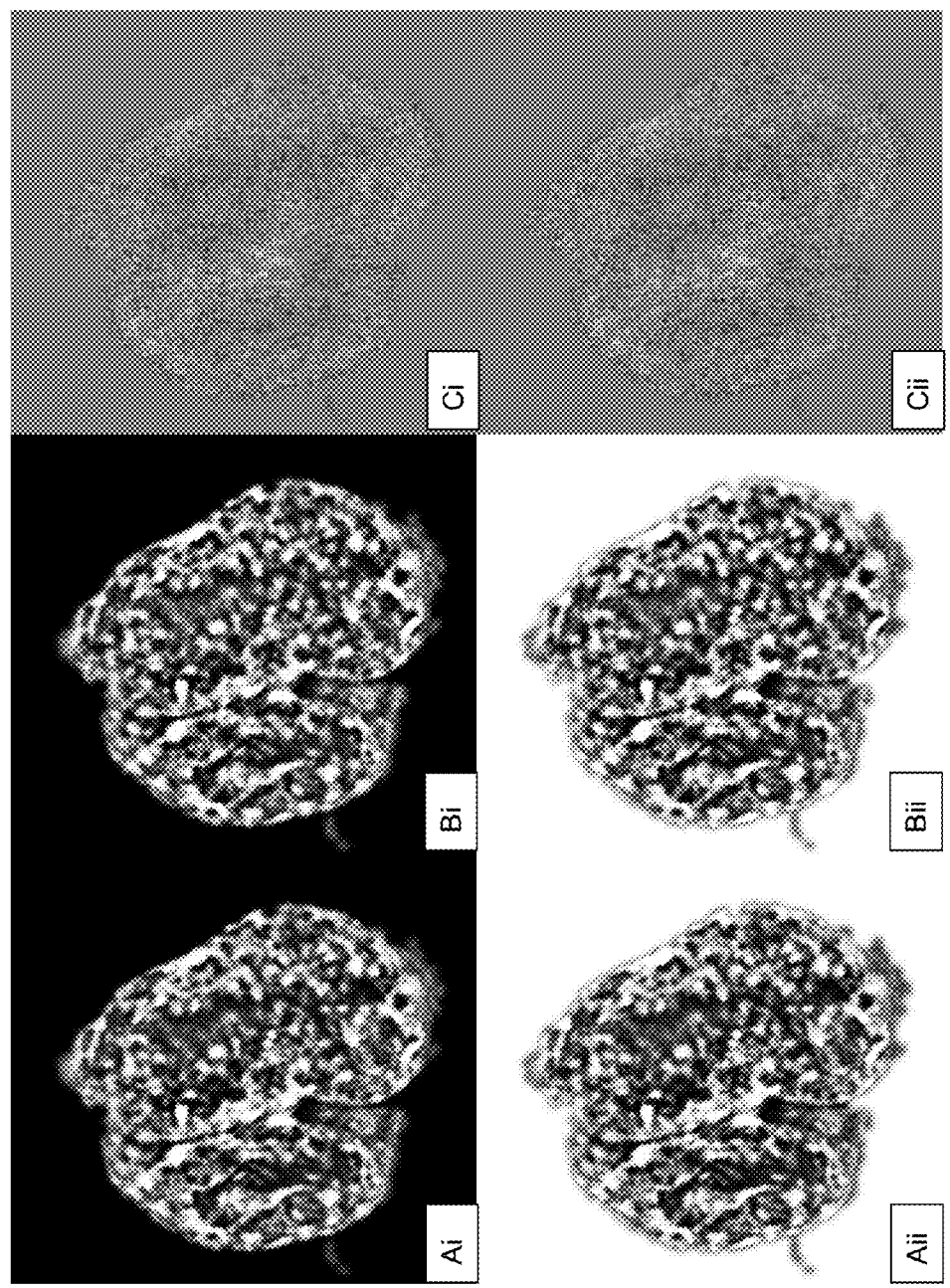

FIG. 14: The top row shows the light image (the structure of the DNA occupied space), the bottom row the dark image (the structure of the DNA-free space). The left column shows the reconstructed SIM image. The middle column is a widefield image on which unsharp masking is applied. The right column shows the difference between the left and middle column. These images clearly show that the same nuclear organization of the DNA is detected using both methods. Both methods may be used as an input for the granulometry process.

Figure 15:
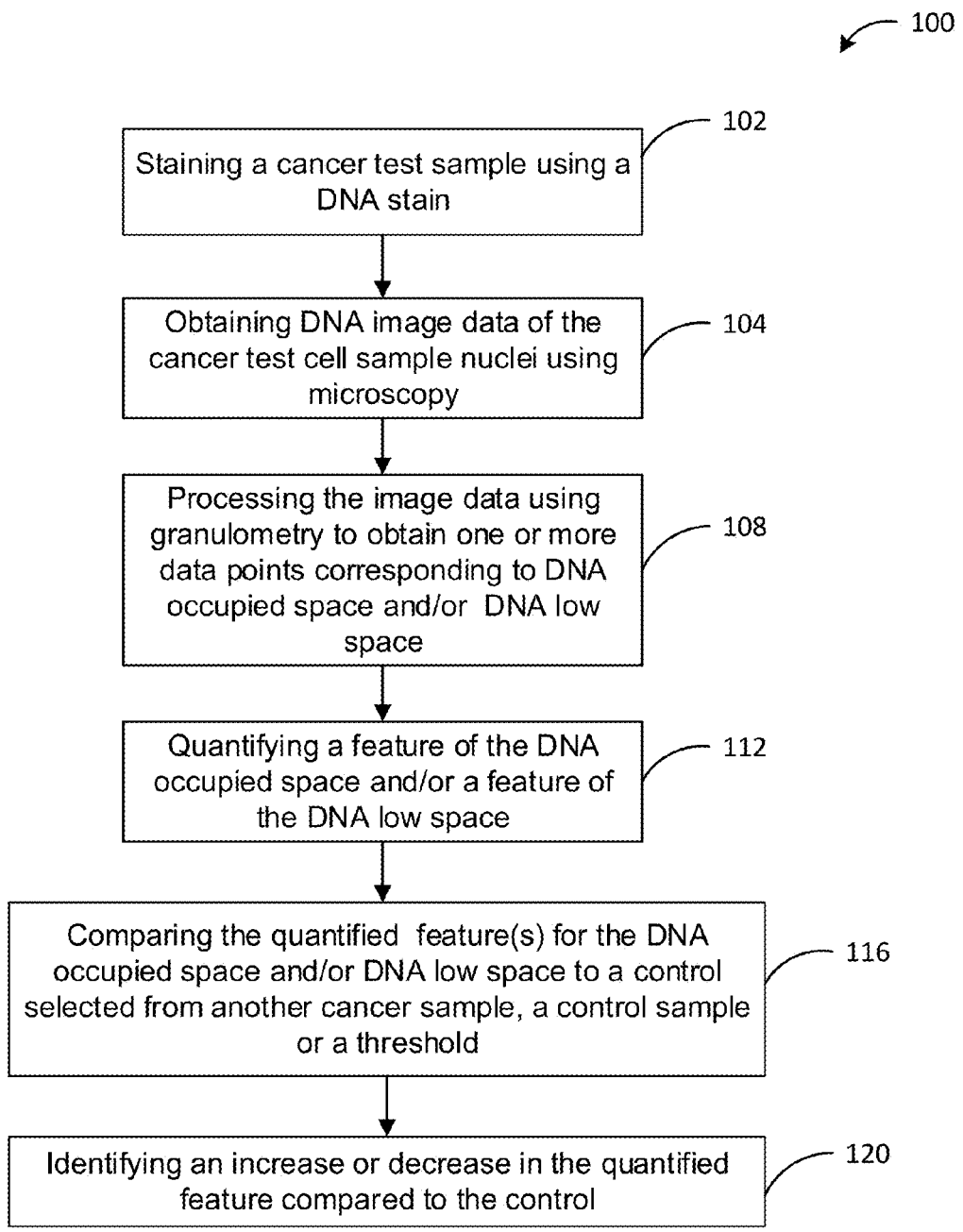

FIG. 15: A flow chart diagram illustrating an example embodiment of a method of measuring a characteristic optionally a cancer characteristic of a cancer test cell sample.

The skilled person in the art will understand that the drawings, described herein, are for illustration purposes only. The drawings are not intended to limit the scope of the applicants' teachings in anyway.

DETAILED DESCRIPTION OF THE DISCLOSURE

It is demonstrated herein that the nuclear organization of DNA inside the interphase nucleus can be visualized with 3D-SIM at microscopic length scales. Visual inspection of 3D-SIM images of different cell types shows qualitative differences in the nuclear organization of DNA between cell types. In order to measure these differences objectively, a method to explore and quantify the nuclear organization of DNA is needed.

It is demonstrated herein that the granularity of the DNA-dye stained (e.g. DAPI-stained) nuclear organization of DNA can then be assessed using 3D-SIM obtained images as described herein. The granularity can also be assessed in the same way from images obtained through other microscope modalities, as a combination of both superresolution microscopy and normal microscopy with image reconstruction algorithms that would lead to similar images as input for the granulometry algorithm.

Definitions

The term "DNA occupied space" as used herein means nuclear space comprising DNA as visualized by a DNA-specific signal. DNA occupied space is apparent for example using "light granulometry" or positive images such as SIM images (e.g. light staining/signals) or modified widefield images as described herein. The term "DNA occupied space" is used interchangeably with the term "DNA structure" and the term "structure of the DNA occupied space".

The terms "DNA low space", "DNA poor space" or "open spaces" as used herein mean nuclear space with low and/or no DNA (e.g. DNA free space) as visualized by a DNA-specific signal, including for example space comprising nucleoli and non-nucleoli comprising space (e.g. determined for example by staining for a nucleoli protein expression, the absence of which indicated that the space is non-nucleoli space). DNA low space is apparent for example using "dark granulometry" or negative images such as negative SIM images (e.g. dark space, devoid of detectable signal) or modified widefield images as described herein. The DNA low space may appear as "holes" which may be round/circular or comprise other shapes. The term "holes" as used herein refer to areas of DNA low space with sizes larger than 1 micron. The term "DNA low space" is used herein interchangeably with the term "DNA free space" and the term "DNA poor space".

The term "intranuclear DNA architecture" or "nuclear organization of DNA" as used herein means all morphological properties of the DNA in a cell nucleus above the quaternary nucleic acid structure and includes for example submicron DNA structures. The term "nuclear organization of DNA" as used herein comprises both "DNA occupied space" and "DNA low space".

Granulometry is an approach to compute a size distribution of structure in greyscale images, using a series of morphological opening operations or morphological sieves. It can be used to measure the nuclear organization of DNA including for example the amount of sub-micron DNA occupied space and the amount of sub-micron DNA low space.

The term "intranuclear submicron DNA architecture" alternatively "submicron DNA structure" or "DNA submicron structure" as used herein means the part of the intranuclear DNA architecture or nuclear organization of DNA smaller than one micron.

The term "length scale" as used herein means a selected range of lengths. The term "length" is used herein to refer to equivalent (e.g. within 10% or within 5%) diameters of the granule-like regions in the DNA occupied and DNA-low/free spaces. In the context of measuring these with a granulometry the term is used as the size (diameter) of the structure element used to measure the structure at that length scale.

The term "DNA size" or "size" (when referring to DNA) as used herein refers to the size of a physical "cluster" visible for example in a 3D-SIM image, rather than a plurality of base pairs of these DNA clusters.

The term "density" as used herein refers to a relative local intensity in images and not the absolute concentration of DNA.

The term "widefield" as used herein means the conventional diffraction-limited microscopy method in which the entire field of view is illuminated at once with equal intensity with a resolution limit that is the ratio of the wavelength of the length over twice the numerical aperture of the objective lens. Embodiments using widefield employ image-processing methods for example unsharp masking and/or deconvolution prior to use as input for the granulometry approach.

The term "superresolution microscopy" as used herein means any microscopy modality which has a resolution lower (e.g. "better") than widefield microscopy.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The terms "about", "substantially" and "approximately" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

The definitions and embodiments described in particular sections are intended to be applicable to other embodiments herein described for which they are suitable as would be understood by a person skilled in the art. For example, in the following passages, different aspects are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Methods and Products

An aspect includes a method of assessing a characteristic optionally a clinical characteristic of a cancer test cell sample comprising:
a. characterizing nuclear organization of DNA of the test cell or tissue sample:
  i. obtaining DNA image data of the cancer test cell sample nuclei;
  ii. processing the image data using granulometry to obtain one or more data points corresponding to DNA occupied space and/or DNA low space;
b. quantifying a feature of the DNA occupied space and/or a feature of the DNA low space.
the cancer test sample.

The method can in an embodiment further comprise:
c. comparing the quantified feature(s) for the DNA occupied space and/or DNA low space to another cancer sample, a control sample or threshold;
d. identifying an increase or decrease in the quantified feature compared to the control (e.g. where the control can be cells from a healthy individual, cells of the same cell type (or lineage) or a value based thereon for example from a population of healthy subjects and/or population same lineage cells);
wherein an increase or a decrease in the quantified feature compared to the control is indicative of the characteristic optionally the clinical characteristic of the cancer test sample.

In at least one embodiment, the cancer test sample may be obtained from a subject. The cancer test sample can be any biological fluid and/or tissue sample comprising cancer cells or suspected of comprising cancer cells. For example, the cancer test sample may be a blood sample. In another embodiment, the cancer test cell sample may be a tissue sample, for example from a biopsy.

In another embodiment, the cancer test cell sample may be a tissue slice, not necessarily consisting of complete cells, in particular a lymph node biopsy. For example, a cancer test cell sample may be a slide comprising cells adhered thereon.

In at least one embodiment, the cancer test sample may be obtained from a subject with or suspected of having a hematological malignancy. In at least one embodiment, the cancer test sample may be obtained from a subject with or suspected of having Hodgkin's lymphoma (HL) or multiple myeloma (MM) or a precursor thereof. In at least one embodiment the cancer test sample may be obtained from a subject with or suspected of having prostate, breast or lung cancer or any other cancer.

In an embodiment, the test cancer sample may comprise a test cancer cells. The test cancer cells may comprise interphase nuclei. The test cancer sample may comprise HL cells such as mono-nucleated Hodgkin (H) cells and/or RS cells and/or optionally differentially nucleated RS cells. In another embodiment, the test cancer sample may comprise multiple myeloma (MM) cells and/or monoclonal gammopathy of unknown significance (MGUS) cells.

In an embodiment, the cancer cell test sample may be stained with a DNA dye for obtaining DNA image data. For example, the DNA stain may be 4',6-diamidino-2-phenylindole (DAPI).

Referring now to FIG. 15, shown therein is a flow chart diagram illustrating an example embodiment of a method 100 of measuring a characteristic optionally a cancer characteristic of a cancer test cell sample. The method may be performed by at least one processor and at least one microscope. In some exemplary embodiments, the steps may be split between at least one processor, a microscope and/or the microscope's processor.

In at least one embodiment, at step 102, a cancer test sample may be stained using a DNA stain. At step 104, a DNA image data of the cancer test cell sample nuclei may be obtained using microscopy. At step 108, the DNA image data may be processed using granulometry. One or more data points corresponding to DNA occupied space and/or DNA low space may be obtained. At step 112, at least one feature of the DNA occupied space and/or a feature of the DNA low space may be quantified.

In an embodiment, the feature quantified may be the density and/or density distribution of the DNA occupied space, optionally submicron DNA structures or micron DNA structures, and/or the DNA low space.

For example, the density distribution may be used to assess whether a particular patient in clinic is likely to relapse. For example, the density distribution may be compared to a threshold. For example, the threshold may be the coefficient of variation or the skewness of the histograms of the density distribution. For example, the threshold may be obtained from at least one earlier sample of the same patient or from at least one other patient with known outcome.

In at least one embodiment, image data of the cancer cell test sample may be obtained (acquired) by capturing at least one image using microscopy. For example, a microscope system may acquire an image and send it to a computing device for further processing. For example, the microscope system may comprise a processor and may therefore process the image itself.

For example, a superresolution microscope may be used. For example, a structured illuminations microscope may be used.

For example, superresolution microscopy and/or widefield microscopy may be used to obtain the image data. The image data may be also obtained using a combination of an optical microscopy method and at least one image reconstruction algorithm. For example, the same microscope may operate both superresolution microscopy and widefield microscopy.

In an embodiment, the superresolution microscopy may be, for example, structured illumination microscopy (SIM), 3D structured illumination microscopy (3D-SIM), airy scan, photo-activated localization microscopy (PALM), or other localization microscopy techniques. There are many localization microscopy techniques that may be used.

For example, in structured illumination microscopy (SIM), an image with a higher resolution than conventional microscopy may be obtained by heterodyne detection in an epi-fluorescent set-up with a periodic illumination pattern.

In at least one embodiment, the image data obtained may be two-dimensional (2D) and/or three-dimensional (3D).

In at least one embodiment, the image data may comprise at least one 2D image. For example, a 2D image may be acquired by capturing a 2D image of a slice of a nucleus in a cancer test sample. For example, a combination of a certain number of acquired cells might be used in a cancer test sample. This number of cells may optionally be or be at least 1, 10, 20 or 30.

In at least one embodiment, a plurality of 2D images may be captured at different depths of the nucleus. For example, the 2D images may be captured in z-planes separated between each other by an interval $\Delta z$, where z-planes as used herein are perpendicular to the z-axis or optical axis of the microscope system. The plurality of the acquired 2D images may form z-stack data (referred herein also as "z-stack"/"z-stacks") and may be then used to reconstruct 3D images. For example, if the 2D images were captured using SIM, the acquired plurality of images may be used to reconstruct 3D-SIM images.

In an embodiment, the image may be reconstructed optionally using ZEN 2012 black edition (Carl Zeiss, Jena, Germany). For example, a selected regularization parameter may be optionally set to $10^{-3}$ and clipping turned off. For example, the regularization parameter may be empirically determined based on a visual inspection of image quality. For example, these settings can be used on a 2D image. For example, these settings can be used for z-stack data.

In at least one embodiment, analyzing the image may comprise selecting a central z-plane. For example, the central z-plane of the nucleus may be selected manually. For example, the central z-plane may be selected manually when the image in that z-plane is visually assessed as being in-focus. For example, the central z-plane may be selected manually by comparing images taken at different z-planes. For example, the z-plane might be selected by an algorithm. For example, the selection algorithm might select the z-plane with the highest image contrast.

In at least one embodiment, the image data captured by the microscope system may be 3D.

Example 1 describes a method wherein 3D-SIM microscopy is used. In an embodiment, the method uses one or more of the steps described in Example 1.

Other superresolution methods, or microscopes that perform optical sectioning, may be used to obtain the usage data.

The image data, obtained with the widefield microscopy may also be used after applying image processing techniques. As discussed in example 4, such image processing techniques may include image sharpening and/or contrast enhancing techniques. For example, unsharp masking may be implemented. The unsharp masking of the image obtained with widefield microscopy may lead to an approximately equally detailed input image for the granulometry as a SIM image. In an embodiment, the processed image is displayed, optionally on a computer display, or similar displaying device. In an embodiment, the image processing is performed prior to processing the image using granulometry.

In at least one embodiment, there is a computerized control system for controlling and receiving data. The computerized control system may comprise at least one processor and memory configured to carry out a method or part thereof described herein.

In at least one embodiment, there is readable storage medium comprising an executable program stored thereon, wherein the program instructs a processor to a method or part thereof described herein.

In an embodiment, the image data may be processed using a computing device and/or computerized control system. For example, the computing device and/or computerized control system may be operably connected to the microscope.

In an embodiment, at least one cell may be automatically detected using isodata thresholding for example in a widefield image or SIM image. Other methods to detect the at least one cell may also be used. In some embodiments involving images obtained using widefield microscopy, grey-scale images may then be error-function clipped between the 10th and 90th percentile of the intensity of the detected cell. In another embodiment, isodata thresholding (also referred to as segmentation) may used with SIM images.

Erf-clipping, a point operation that may shape a linear edge region into a scaled error function, may be applied. Different clipping methods/function would likely result in similar results. One would fine tune the specific function and values used to the specific application.

Processing the image data and/or analyzing the image data comprises measuring granulometry. The granulometry measures the size distribution of the elements of the image. For example, granulometry of the DNA occupied space and the DNA low space of the image may be measured. The granulometry of the DNA occupied space may be obtained by measuring "light granulometry" which implies measuring granulometry of a positive image. The granulometry of the DNA low space may be obtained by measuring "dark granulometry" or measuring granulometry of a negative image.

For example, the granulometry may be measured using a morphological sieve applied to the image data. For example, the morphological sieve may be applied to either clipped or unclipped images. For example, the granulometry may be measured using a segmentation method, as described, for example in example 3.

In an embodiment, processing the image data and/or analyzing the image data may comprise determining an intensity histogram of the image. For example, the intensity histogram's skewness and coefficient of variation may be determined.

In an embodiment, a difference in the skewness of the analyzed image compared to a control skewness may be indicative of a poor clinical characteristic. For example, as shown below, malignant HL cells may have a more asymmetric DNA distribution than lymphocytes. For example, for the 3D-SIM image, the skewness of both the H and RS cells may be higher than that for the lymphocytes.

The difference in skewness compared to control skewness may be, for example, an increase or decrease in skewness. An increase in skewness in a HL sample may be, for example, indicative of RS cells.

In an embodiment, the image data either prior to processing and/or analyzing or post processing and/or analyzing is displayed on a computer display or other similar device.

In an embodiment, the method may further comprise calculating values of a cumulative distribution function (CDF). In an embodiment, the method may further comprise calculating at least one value of a probability density function.

In an embodiment, a ratio of DNA occupied to DNA low space may be calculated. For example, the fraction of the nucleus that contains DNA compared to no DNA may be used to estimate N in a Kolmogorov-Smirnov (KS) test. A method to estimate the numerator and denominator of such a fraction is described in Example 1 (section "Estimating the number of objects") and can be used to calculate the ratio.

In an embodiment, the measurements of the DNA structure and the DNA low space were performed on the entire nucleus or a portion of the nucleus. For example, the portion of the nucleus may be a z-plane or a part of a z-plane, for example between about 50% and about 100%, between about 60% and about 90%, and/or, between about 70% and about 100% of a z-plane.

In an embodiment, the feature quantified by the method may be the size distribution of length scales of the DNA occupied space and/or the DNA low space. For example, a cumulative distribution of sizes of DNA architecture features for a cell nucleus may be determined.

In an embodiment, the feature quantified may be the density and/or density distribution of the DNA occupied space, optionally submicron DNA structures or micron DNA structures, and/or the DNA low space.

In an embodiment, the method further comprises measuring a nucleoli constituent, optionally upstream binding factor (UBF) or another protein present in nucleoli or nuclear bodies. Immunological methods can be used to detect the nucleoli or nuclear body protein for example UBF as described in Examples 1 to 5.

In at least one embodiment, it is possible to detect changes (differences) in the DNA architecture as well as size distribution when the samples are compared to normal cells or a different cancer sample. In at least one embodiment, comparing one sample to another can be used for providing a clinical characteristic of the cancer sample, such as, for example, diagnosis. For example, a sample with an earlier cancer sample from the same patient or an earlier stage or later stage control may be compared in order to provide the clinical characteristic.

Referring again to FIG. 15, in at least one embodiment, at step 116, the quantified feature(s) for the DNA occupied space and/or DNA low space may be further compared to a control selected from another cancer sample of known outcome, other control sample, optionally an internal control, or a threshold based for example on a population of control samples. At step 120, an increase or decrease in the quantified feature, compared to the control, may be identified.

In an embodiment, a change for example an increase in DNA low space negative for a nucleoli constituent is indicative of a poor clinical feature.

As demonstrated, differences in nuclear architecture and the number and size of "holes" may be visible in HL samples. Differences in MM and MGUS compared to normal cells may be also demonstrated.

In an embodiment, cancer test sample comprises mononucleated Hodgkin's lymphoma cells and/or multinucleated Reed Sternberg (RS) cells. As described in the examples, differences in nuclear architecture and the number and size of "holes" may be visible from bi- to tri- to tetra-nucleated (and multinucleated) RS cells.

In an embodiment, a decrease or increase in the size of DNA low space compared to a normal cell is indicative of a Hodgkin's lymphoma (HL). For example, a change in nuclear DNA distribution and any significant variation from the normal cells of the same lineage may be indicative of HL.

Differences in length scales are noted for cancer and non-cancer cells. In an embodiment, the difference between the distribution between Hodgkin's test cell and control is detected at a length scale of about 0.6 μm to about 2 μm.

For example, the values of distribution may be obtained and compared for a specific length scale, for a group of specific length scales, and/or for a length scale within a certain range. For example, the distribution may be compared for the length scale range of about 0.6 microns to about 2 microns, about 0.7 microns to about 2 microns, 0.5 microns to about 3 microns. For example, the distribution may be compared for a specific length scale of 0.5 microns and/or 0.6 microns. Any range between about 0.6 microns and 2 microns, or about between 0.6 microns and less than 1 micron may be used in other embodiments.

In an embodiment, an increase in the number of submicron DNA structures, optionally DNA structures that are approximately 200 to approximately 700 nm, is indicative of a poor clinical characteristic.

In an embodiment, an increase in the number of micron DNA structures of approximately 1 micrometer to approximately 3 μm is indicative of a poor clinical characteristic. Other features are described in Example 1.

In an embodiment, the method may be used for identifying the number and/or proportion of H and/or RS cells, and/or optionally differentially nucleated RS cells.

In the Examples, results are also provided for multiple myeloma (MM) and monoclonal gammopathy of unknown significance (MGUS) cells.

As shown in Example 2, the method described herein permitted to determine significant change in submicron DNA structure and a change in DNA-low space compared to normal lymphocyte nuclei. For example, change in submicron DNA structure and/or submicron DNA-low space may be either an increase or decrease compared to normal lymphocyte nuclei, depending on a type of cancer. For example, a significant increase in submicron DNA structure and an increase in DNA-free space compared to normal lymphocyte nuclei are shown herein in the Examples below.

As shown in Example 2, the method described herein permitted to determine significant differences in nuclear DNA organization and size distribution of nuclear DNA between MM and MGUS cells. For example, the method described herein permitted to determine that MGUS nuclei may have significantly more DNA-free space than MM nuclei.

As shown in Example 3, the method described herein permitted to determine that the DNA structure may be significantly different at the 5% level between RS cells of non-relapsed and relapsed patients. For example, the RS cells of relapsed patients have a larger relative amount of finer (smaller) DNA structure. Therefore, the RS cells of patients entering long lasting remission and of relapse patients may differ significantly.

For example, the upstream binding factor (UBF) may be stained. UBF is a protein that is present in the nucleolus. Such staining may help to determine whether the DNA-free space might be associated with nucleoli.

The granulometry results may also be classified based on the CDF value. For example, the CDF for the DNA structure of RS cells may be compared for relapsed cases and cases with remission. As shown in Example 4, the relapsed cases may have higher value of CDF calculated for the DNA structure of RS cells than the CDF value for the cases with remission. Therefore, CDF values for one or more diameters of the DNA structure may be used to classify the cells. For example, CDF values at a certain diameter of the DNA structure may be compared to other available CDF values of the same diameter in order to determine whether the case will result in remission or relapse.

In one embodiment, the method may comprise determining whether the cancer test cell sample, obtained from the patient, comprises RS cells, which have cumulative distribution function (CDF) of a submicron structure of DNA low space being above or below a selected threshold. Similarly, the method may also comprise determining whether the cancer test cell sample, obtained from the patient, comprises RS cells, which have cumulative distribution function (CDF) of a submicron structure of DNA occupied space being above or below a selected threshold.

As discussed in Example 4, the selected threshold (or cut-off value of CDF) may be determined by obtaining the image data for a plurality of cancer test samples of a group of patients with known remission or recession outcome. The image data may be processed or analyzed using granulometry and CDF values of the submicron diameters of the DNA occupied space and/or DNA low space may be obtained. The plurality of CDF values obtained may be further analyzed using one or more classification techniques to determine the selected threshold for CDF values for the likelihood of the patient's remission. Similarly, the plurality of CDF values may be analyzed to determine the selected threshold for CDF values for the likelihood of the patient's recession.

For example, the values of CDF and therefore values of the selected threshold or thresholds may be determined for a specific diameter of the submicron structure of DNA occupied space and/or DNA low space. As shown in Example 4, the diameter (length/size) of the submicron structure of DNA occupied space and/or DNA low space may be optionally 500 nm.

In an embodiment, if the CDF is below the threshold, it may be determined that the patient will be more likely in remission. If the CDF is above the threshold, it may be determined that the patient will be more likely in recession.

For example, it may take around 5 minutes for one DNA image to be taken. For example, the analysis may take about 5 minutes per cell.

Although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

The methods described herein can be used for diagnosis, to monitor progression, disease transition, disease subgroup, treatment efficacy, optionally after surgery, radiation or other treatment, for assessing cancer heterogeneity and/or for clinical trial group assignment. Changes in nuclear architecture as described here can be indicative of disease, stage, disease subgroup, progression or disease transition and/or amelioration.

In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way but rather as merely describing the implementation of the various embodiments described herein.

The exemplary embodiments are described herein with reference to various algorithms, modules, methods, calculation units, circuits and architectures. It will be understood that such algorithms, modules, methods, calculation units, circuits and architectures can be implemented in hardware or machine, such as in electrical and/or electronic circuits, according to various methods known in the art. For example, and without limitation, embodiments described herein may be implemented on or embedded within a microchip, microprocessor, co-processor, programmable logic, field programmable gate array (FPGA) central processing unit (CPU), graphics processing unit (GPU), Accelerated processing unit (APU), system-on-chip (SOC) and/or application specific integrated circuits (ASICs). For example, where the embodiments are implemented as a co-processor, the co-processor can be coupled to or integrated with a processing unit in which certain operations required by the processing unit can be offloaded to the co-processor.

In some embodiments, the systems and methods as described herein may also be implemented as a non-transitory computer-readable storage medium configured with a computer program, wherein the storage medium so configured causes a computer to operate in a specific and predefined manner to perform at least some of the functions as described herein.

The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, internet transmissions (e.g. downloads), media, digital and analog signals, and the like.

The various embodiments of the systems and methods described herein may be implemented in hardware or software, or a combination of both. For example, some embodiments may be implemented in computer systems and computer programs, which may be stored on a physical computer readable medium, executable on programmable computers (e.g. computing devices and/or processing devices) each comprising at least one processor, a data storage system (including volatile and non-volatile memory and/or storage elements), at least one input device (e.g. a keyboard, mouse or touchscreen), and at least one output device (e.g. a display screen, a network, or a remote server). For example, and without limitation, the programmable computers may include servers, personal computers, laptops, tablets, personal data assistants (PDA), cell phones, smart phones, and other mobile devices. Program code can be applied to input data to perform the functions described herein and to generate output information. The output information can then be supplied to one or more output devices for outputting to one or more users.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Malignant cells in HL are mononucleated Hodgkin cells (H) and bi- or multinucleated Reed-Sternberg cells (RS). The RS cell is the diagnostic cell for this malignancy. A variety of cellular functions are affected in these cells in comparison to the lymphocytes from which they originate [Kuppers et al., 2012]. A multitude of translocations have been identified in RS cells [MacLeod et al., 2000] and their nuclear architecture becomes progressively more disorganized as the number of subnuclei increases [Guffei et al., 2010; Knecht et al., 2009]. This includes an increase in the number of centrosomes [Martin-Subero et al., 2003].

The size distribution of DNA structure and the DNA-free space(s) (e.g. DNA low) in lymphocytes, H cells and RS cells are quantitatively described herein. The differences between the DNA structure and the DNA-free space(s) in lymphocytes, H cells and RS cells are assessed.

It has been also investigated herein a spatial relation between the nucleolus-related protein UBF and the DNA-free space. A significant and progressive difference has been found in DNA structure and DNA-free space among normal, Hodgkin and Reed-Sternberg cells.

Materials and Methods

Cell Preparation

Normal blood was treated with Ficoll (GE Healthcare, Uppsala, Sweden) to obtain the control lymphocytes. The removed buffy coat was washed in a PBS solution and the cell pellet collected. The cells were subsequently placed onto slides. The HDLM-2 cell line [Drexler et al., 1986] was grown in RPMI-1640 medium, supplemented with 20% Fetal Bovine Serum (FBS), 1% L-glutamine, and 1% penicillin-streptomycin (reagents from Invitrogen/Gibco, Burlington, ON). Cells were incubated at 37° C. with 5% CO2 in a humidified atmosphere. After 2 days, 1-2 ml of fresh media was added. The following day, half of the cells were split into a fresh plate; the other half were used to prepare slides. The slides, both the control and HDLM-2 slides, were incubated in 3.7% formaldehyde (Sigma-Aldrich, Oakville, ON) for 10 minutes. The slides were dehydrated using a standard ethanol series, air dried and stored at −20° C. until needed. The slides were later rehydrated using a reverse ethanol series and permeabilized with 0.2% Triton X-100. Primary UBF anti-body (H-300, sc-9131, Santa Cruz, Dallas) was used at a concentration of 1:60 and incubated for 45 minutes at room temperature (RT). Slides were washed in 1×PBS/50 mM $MgCl_2$ and UBF was visualized with goat-anti-rabbit Alexa 488 (Molecular Probes, Eugene, Oreg.) at a concentration of 1:500 and incubated for 30 minutes at RT. Slides were then washed in 1×PBS/50 mM MgCl2 and 50 µl of 1 µg/ml DAPI (4',6-diamidino-2-phenylindole) was added and incubated for 5 minutes. Excess DAPI was drained, 1 drop of Vectashield (Vector Labs, Burlingame, Calif.) was added to the slide and a coverslip (No. 1½, Schott, Mainz, Germany) was placed and sealed with nail polish. Slides were stored at 4° C. until imaging.

Microscopy

The cells were recorded with a Zeiss Elyra PS1 SIM equipped with a Plan-Apochromat 63×/1.40 Oil immersion objective using an Andor EM-CCD iXon 885 camera and a 1.6× tube lens at room temperature. The DAPI channel was obtained with 405 nm laser excitation, 23 µm diffraction grating and filter cube SR Cube 07; the UBF channel with 488 nm laser excitation, 28 µm diffraction grating and filter cube SR cube 11.

The lateral pixel size, $\Delta x$ and $\Delta y$, was 79 nm in the recorded images and 40 nm in the reconstructed image, the step between z-planes, $\Delta z$, was 91 nm. The 3D-SIM and widefield images were reconstructed with ZEN 2012 black edition (Carl Zeiss, Jena, Germany) with the standard settings except for the regularization parameter, which was set to $10^{-3}$, and clipping, which was turned off. The regularization parameter was empirically determined based on visual inspection of image quality. The regularization parameter was set to find the trade-off between minimizing noise and image artifacts while maximizing the image resolution. Clipping the image in the reconstruction stage artificially sets the background to zero (black), but hides actual image information and was, therefore, not done.

Image Analysis

The image processing and measurement steps were performed in Matlab (MathWorks, Natick, Mass.) with the toolbox DIPimage [Luengo Hendriks et al., 1999]. A central z-plane was manually selected for processing (see below). The cell was automatically detected (also referred to as segmentation) by isodata thresholding [Ridler and Calvard, 1978] the widefield DAPI image and filling the holes in the binary image. For example, other methods to detect the cell may be used. The greyscale DAPI images were error-function clipped between the 10th and 90th percentile of the intensity over the detected cell [Verbeek and van Vliet, 1993].

The granulometry of the DNA structure and DNA-free space was subsequently measured with a morphological sieve applied to the unclipped images [Luengo Hendriks et al., 2007]. The coefficient of variation (the standard deviation divided by the mean) and skewness of the intensity histogram over the detected region was computed as well. Granulometry is an approach to compute a size distribution of structure in greyscale images, using a series of morphological opening operations or morphological sieves. It can be used to measure the nuclear organization of DNA including for example the amount of sub-micron DNA occupied space and the amount of sub-micron DNA low space.

To assess the significance of the measured difference, two-sided, two-sample Kolmogorov-Smirnov (KS) tests have been used. In these KS tests the sample size was determined by the relative area over the median structure size (see below for details). A linear classification line based on the Fisher linear discriminant assuming equal priors was performed for the histogram features using the PRTools toolbox for Matlab [Duin et al., 2007]. The significance of differences in the classification error was assessed with the McNemar test. For each apparent hole in the SIM DAPI image (FIG. 1) it was determined by visual inspection whether or not it was filled with UBF. Pearson's correlation coefficient, R, was calculated over the nucleus between the DNA-free space, the negative of the DNA image, and both the original unclipped SIM and widefield UBF images. The significance of the differences between the UBF-based measures was assessed with the two-sample Student t-test with unequal variances.

Two-Dimensional Granulometry from a Three-Dimensional Image

In clinical samples it is common to work with tissue sections rather than full cells, so it should be advantageous to be able to do all measurements on 2D slices rather than the full 3D cells even though presently the full cell images are available. Granulometries are also computationally intensive operations, especially for large 3D images with non-rectangular structure elements. To judge whether it is possible to replace the 3D image by a 2D-slice, the effect of using a central two-dimensional slice instead of the full three-dimensional image as input to the granulometry by performing a simulation has been assessed. A 256×256×64 image was created with randomly placed 2500 blobs (which can be seen as a simple model for small DNA clusters) in an ellipsoid (resembling the cell nucleus) with semi-axes of 100 pixels in the lateral directions and 25 pixels in the z direction. The center position for each blob was randomly selected from a uniform distribution for each cardinal direction; the position was reselected if it would have been placed outside of the ellipsoid. Each blob has the shape of the point spread function of a high-NA fluorescence microscope [Gu, 2000]. This artificial image was taken as the 3D input image. The randomly-selected "central" z-slice of this image was taken as the 2D image. See FIG. 5(Ai) for a central slice; see FIG. 5(Aii) for an (x,z)-slice of the 3D image. The granulometry was measured for both the 2D and 3D image as for the cell images in the Materials and Methods. In particular, an isotropic structure element was used with the granulometry function of DIPimage [Luengo Hendriks et al., 1999—; Luengo Hendriks et al., 2007].

The resulting size distributions for both the blob structure and the blob-free space are plotted in FIG. 5(Aiii-iv). Both distributions overlap for small length scales (less than 5 pixels). The granulometry on the 2D slice measures a relatively higher number of large objects than the 3D granulometry. This is caused by the anisotropic nature of this image. In-focus objects in the 2D slice have the same size as for the 3D image, in which the central part of the blob is dominant. Out-of-focus objects appear to be larger, as illustrated in FIG. 5(Ai). The out-of-focus blobs appear as objects of a larger scale, whereas in the 3D image their size is still given by the same smaller central size. Due to optical sectioning in 3D-SIM this effect is smaller than for a widefield image, which strengthens the case for using a central 2D slice. A smaller shift occurs for the dark image, which is associated with the blob-free space. This illustrates how the granulometries of the foreground and background are not complementary. In this case the shift is caused because the spacing between dots in the z-direction is smaller than in the x and y directions, because of the anisotropy of the blobs.

Granulometry does not necessarily yield the same size distribution using 2D and 3D images. The differences between size distribution in 2D and 3D may be explained by the inherent anisotropy of the image. Because the axial and lateral directions are fundamentally different in microscopy, sizes need to be interpreted differently in these directions. This means that an isotropic, spherical structure element (either in equal physical length or equal pixel number) in the granulometry does not weigh the lateral and axial directions fairly.

Despite the described differences between granulometry results for 2D and 3D images, 2D images may be used instead of 3D images. The 2D granulometry may provide a reduced computational load compared to the 3D granulometry. Moreover, the measurements may be applied to cell slices from clinical samples. Therefore, the size distribution of both the DNA structure and DNA-free space in 2D slices were measured through the center of biological cells.

Estimating the Number of Objects

The two-sided, two-sample Kolmogorov-Smirnov test yields the probability that two empirical cumulative distributions functions (CDF's) are drawn from the same underlying distribution.

The p-value is based on the maximum of the absolute difference of the CDF's and the number of elements N on which each distribution is based. The granulometry measures the size distribution of the elements of an image. It does not, however, count objects, so there is no explicit measure of N obtained in the granulometry. As no straightforward "counting method" (counting of objects) may be available, the number of elements N needs to be estimated otherwise.

Taking N as the number of pixels would ignore the existence of objects which give rise to a high correlation between neighboring pixels in the image.

In the case of a finite number of non-overlapping disks of the same size and the same intensity, the granulometry will result in a step function at the size of the diameter of the disks. The number of objects may be estimated, for example, by dividing the total sum of object pixels by the area of the disks. The diameter is also the size for which the granulometry crosses the 50 percentile, i.e. the median size of the distribution with respect to area (volume) coverage. In general, the intensities of the objects might fluctuate and the size distribution will resemble a log-normal distribution.

The number of objects may be estimated from the median of the granulometry. In particular, circular granules with a diameter d may be used. When the median value of the granulometry is $d_{med}$, then the area of this granule may be calculated as $A_{med}=\pi d_{med}^2/4$ The total area A of the nucleus may then be divided into a light part and a dark part, representing the relative area of both of the complementary images. This can be achieved by normalizing the image by linearly stretching it between 0 and 1 inside the nucleus. The relative light area $A_{light}$ is given by the sum of this normalized image over the nucleus. The relative dark area is given by $A_{dark}=A-A_{light}$. The approximate number of objects may then be calculated as $N_c=A_c/A_{med,c}$, where c can be substituted by either light or dark.

To assess this method, 1000 images were randomly created. Each image was a 1024×1024 image in which 600 circular Gaussian blobs were randomly placed. These blobs were placed in a circle with a radius of 300 pixels and their center positions were randomly drawn from a uniform distribution. The standard deviations σ of each Gaussian blob was randomly drawn between 2 and 4 pixels for each blob. See FIG. 5(Bi) for an example of one of these generated images.

The image was processed with the granulometry in the same manner as the cells as described in the Materials and Methods. The input image for the light granulometry for the same test image is shown in FIG. 5(Bii). For each of the light images the number of objects was estimated based on the median granule size as described in the previous paragraph. The granulometry image was segmented using an isodata threshold [Ridler and Calvard, 1978]. The resulting number of unconnected areas was counted as an alternative to estimate the number of objects. See FIG. 5(Biii) for a labeled image in which each area is color coded.

Some of the objects overlapped in the images. This may mean that even though 600 Gaussian blobs were placed, not all of them can be seen as a separate object.

For all 1000 random images, the number of objects was estimated using two methods. Counting objects in the segmented image led to a sample mean of 348±12. The estimation of the number of objects based on the granulometry led to a sample mean of 458±12. The ratio of the objects estimated over the objects counted had a sample mean of 1.32±0.06.

The p-value in the Kolmogorov-Smirnov test may be determined by the quantity $\sqrt{N_1N_2/(N_1+N_2)}D$, with $N_1$ and $N_2$ the sample sizes of both distributions and D the maximum of the absolute difference of both cumulative distribution functions [Young, 1977]. When the Smirnov distribution [Kim, 1969] is taken as a first order approximation, then the p-value becomes:

$$p \approx \sqrt{1/2}\sqrt{\log 2 - \log(1 - N_1N_2/(N_1+N_2)D)}. \quad (1)$$

Note that the full distribution was used in this study, rather than this approximation to calculate the p-values. Because the p-value scales with the order log(N), the estimate for N is valid when it has the right order of magnitude. The 32% difference between the estimation method and the counting method means that this estimate is reasonable. Indeed, it may be assumed that to be reasonable, N estimated needs to be not more than 2 times higher than N counted or N counted needs to be not more than 2 times higher than N estimated. Therefore, the difference of 32% is reasonable.

A different method of estimating the number of objects could lead to a different number of objects; the granulometry based method is, however, independent of interpretation of the objects and only based on the size distribution. Note that no counting method would be viable for the cell images, because there are no distinguishable individual objects.

All these reasons combined means that using the median-based estimate for N may be a valid number to use in the Kolmogorov-Smirnov test.

It should be noted that the number of objects N may be estimated using similar estimation methods.

Results

DNA Structure and Structure of DNA-Free Space

In order to investigate the DNA structure, lymphocytes were isolated and imaged using 3D-SIM, see FIG. 1A for the recorded DAPI channel of a typical lymphocyte (L). The widefield image does not reveal details of the DNA distribution within the nucleus. Structure in the DNA distribution within the nucleus becomes visible in the 3D-SIM image, although it is still mostly a relative uniform distribution for normal lymphocytes, with some intensity variation in the middle of the nucleus.

To assess the DNA distribution within the nucleus and to determine whether there are differences between normal and cancer cells, Hodgkin lymphoma (HL) cells were studied, where mono-nucleated Hodgkin (H) cells give rise to bi- or multinucleated Reed Sternberg (RS) cells. The spatial distribution of the genome in RS cells may become progressively more disturbed with increasing multinuclearity [Guffei et al., 2010].

Images of H and RS cells from the HL cell line HDLM-2 were recorded. Several representative images are shown in FIGS. 1 and 4. Although some structure variations are visible in the widefield images, all 3D-SIM images reveal more of the internal DNA structure than the respective widefield images of the same cells.

Several qualitative observations can be made. The DNA structure inside the nuclei shows some granularity, i.e. it is non-constant and shows structure at smaller length scales than the open spaces. There are "holes" in the DAPI stained nuclei. These "holes" are areas within the nucleus that have a low DNA density—or contain no DNA at all—as exemplified by the arrows in FIG. 1. Note that such large scale open areas are rare in lymphocytes.

The granulometry was used to quantify the distribution of length scales present in the DNA structure as well as the DNA-free space, the dark regions in the figures. The resulting cumulative distributions of the typical granule sizes in these cells are plotted in FIG. 2A, B for the three cell types. The granule size distribution of the DNA distribution is smallest for the control lymphocytes. Both HL cell types contain relatively more DNA structures at both the low end of the size distribution scale, 200-700 nm, representing the actual intranuclear DNA structure, and the high end of the size distribution in these images, 1-3 μm, representing structure with length scales close to the size of the cells.

The significance of the measured differences was evaluated with the two-sided, two-sample Kolmogorov-Smirnov test (KS-test) for triplicate experiments and found the differences to be significant at the 5% level. The triplicate experiments were then combined for a total cell count of 137 lymphocytes, 129 H cells and 97 RS cells.

The KS-test determined that all three groups were significantly different, $p=10^{-18}$ for L vs. H cells and L vs. RS cells, $p=10^{-11}$ for H cells vs. RS cells. The length scales measured by the granulometries are mostly larger than the traditional microscopic diffraction limit. The structure itself is hard to detect visually in the widefield images (FIGS. 1 and 4) and is not picked up by the granulometry when applied to these images (FIG. 7).

In the widefield case, the granulometry measures highlight differences in the global size of the cell (3-15 μm) rather than the intranuclear DNA structure. The differences are, however, also significant for the widefield images: $p=10^{-12}$ for L vs. H cells, $p=10^{-37}$ for L vs. RS cells and $p=10^{-7}$ for H. vs. RS cells. But again, the differences occur at length-scales on the order of the size of the nuclei, rather than the size of the intranuclear structure for the widefield images.

The DNA-free space was characterized to investigate whether there are changes between normal and cancer cells. The control lymphocytes contained DNA-free space at larger length scales; this is also visible in the cell images (FIG. 1). Both the H and RS cells displayed smaller open areas/holes than lymphocytes. The largest difference between the distributions occupied at the length scales of 0.6-2.0 μm. These are the typical sizes of the DNA-free space as well as the "holes" visible in the DAPI-stained images (FIG. 1).

Neither the DNA structure, nor the DNA-free space show apparent differences in the widefield image. For example, the differences are not apparent when images are visually inspected.

Upon measurement, a significant difference occurs at the size of a whole cell (e.g., not reflective of intranuclear differences). The difference in the DNA-free space is, however, significant for the 3D-SIM image; the KS-test yields $p=10^{-20}$ for L. vs. H cells, $p=10^{-10}$ for L vs. RS cells and $p=10^{-7}$ for H. vs. RS cells. For the widefield images, shown at FIG. 7, these measurements are: $p=10^{-34}$ for L vs. H cells, $p=10^{-86}$ for L vs. RS cells and $p=10^{-23}$ for H. vs. RS cells. Again, the differences occur at length scales on the order of the size of the nuclei, rather than the size of the intranuclear structure for the widefield images.

It was also noted visually that there was a difference in the DAPI intensity over the nucleus. The intensity histogram itself has different properties for the different cell groups (3D-SIM, FIG. 2C,F; widefield, FIG. 7C,F). When the coefficient of variation (c.o.v.) and skewness are plotted for each cell there is no correlation between these measures for the 3D-SIM image (R=0.065). These measures are, however, somewhat correlated in the widefield image (R=0.500). Since the three cell groups seem to occupy somewhat different regions of the 2D space spanned by c.o.v. on one axis and skewness on the other axis, the 2D space was linearly divided between the cell groups. If there were no difference between the cell types, the resulting discrimination functions would not be meaningful and ⅔=67% would be classified erroneously. Classifying the cells based on their histogram, the error rate was 30% for the 3D-SIM images and 38% for the widefield images. Most of these errors occur close to the boundary lines between the regions. This is expected, because a transition from H to RS cells may be seen. The error rate of the classification decreases significantly for the SIM images compared to the widefield images (p=0.021). For the 3D-SIM image the skewness of both the H and RS cells is higher than for the lymphocytes.

UBF Content in the DNA-Free Space

For the HL cells, both H and RS, some "open spaces" (FIG. 1) are clearly visible. These open spaces do not appear in the control lymphocytes. Nucleoli display the same morphology and would also be associated with a lower DNA concentration. To investigate whether the DNA-free space might be associated with nucleoli, the upstream binding factor (UBF) was stained. UBF is a protein that is present in the nucleolus [Hein et al., 2013]. The spatial position of UBF within the nucleus is depicted for its widefield image in FIG. 3. FIG. 8 shows the SIM UBF image. Areas with higher concentrations of UBF do occur in some of these holes, but not in all of them. For the HL cell line, it was counted how many of these holes are filled with UBF and how many are not. It was found that 85% of the holes in the H cells were filled with UBF, compared to 50% of the RS cells (FIG. 3G). This difference is significant ($p=10^{-12}$). To assess this, Pearson's correlation coefficient of the DNA-free space (the negative of the DAPI image) and the UBF image was calculated. The correlation coefficient between the SIM UBF image and SIM DNA-free space (FIG. 3E) was computed first. The coefficient was relatively low (between 0.05 and 0.14), because the UBF signals in the 3D-SIM images appear very spiky and not as homogeneous as in the widefield images. The correlation between both channels, however, monotonically decreases from the control lymphocytes to H cells to RS cells. This indicates an increase in DNA-free space that is not occupied by this transcription factor. This is also exemplified by the correlation coefficient between the SIM DNA-free space and the widefield UBF image (FIG. 3F), in which the UBF signal appears spatially homogeneous. The correlation coefficient again decreases, from 0.38 for the lymphocytes through 0.27 for the H cells to 0.18 for the RS cells. The difference between the lymphocytes and the H and RS cells are significant in all cases (L vs. H: $p=10^{-5}$ for DAPI-SIM and UBF-SIM, $p=10^{-8}$ for DAPI-SIM and UBF-widefield; L vs. RS: $p=10^{-7}$ for DAPI-SIM and UBF-SIM, $p=10^{-14}$ for DAPI-SIM and UBF-widefield). The difference between H and RS cells is also significant for the correlation between the SIM DNA-free space and the SIM UBF image (p=0.029) as well as for correlation between the SIM DNA-free space and widefield UBF image ($p=10^{-6}$).

Progressive Trend with the Population of Reed-Sternberg Cells

Because RS cells can consist of different numbers of subnuclei, which form progressively during tumor development, this study compared binucleated Reed-Sternberg (RS2) cells with RS cells that contain four or more subnuclei (RS4+). Both groups consisted of 36 cells in this study; the remaining 25 cells were trinucleated RS cells. The same measurements were performed on this two-group system.

The DNA structure is different between the two (KS-test $p=10^{-5}$), in particular the RS4+ cells had a larger spread in the size of their structure than the RS2 cells. The differences for the DNA-free space were, however, not significant (KS-test, p=0.09). For the widefield images this led to p=0.0016 for the DNA structure and $p=10^{-9}$ for the DNA free space. The 2D c.o.v.-skewness space classification leads to a 25% error rate for the SIM images and a 35% error rate for the widefield images.

As before, the error rate decreased for the SIM images compared to the widefield images; although not significantly (p=0.18). Note that this is a two-group system in which complete overlap would mean a classification error of 50%. The differences between RS2 and RS4+ cells display the same trend as the differences between H and RS cells. The UBF-based measures revealed differences as well, although not significant in all cases. The relative number of "holes" that is filled with UBF is 69% for the RS2 cells and 41% for the RS4+ cells, a significant difference ($p=10^{-5}$). The difference in the mean correlation coefficient between the two groups was significant when comparing the DNA-free space in SIM with the widefield UBF image (p=0.021). The difference between RS2 and RS4+ cells was, however, not significant when the correlation coefficient was calculated between the UBF and DAPI SIM images (p=0.22). The RS4+ cell were not further subdivided into subgroups of tetranucleated cells and cells with 8 or more subnuclei.

Discussion

The intranuclear DNA structure of normal and cancer cells using a superresolution microscopy method has been described. The DNA structure revealed by high resolution light microscopy has been quantified. In particular, structures at the 200-700 nm size range were measured. It was observed that many more of these sub-micron structures are present and that they are smaller in size in HL cells than in control lymphocytes.

An increased skewness for the HL cells was noted when the properties of the SIM DAPI intensity histograms were measured. This means that these malignant cells have a more asymmetric DNA distribution than lymphocytes. This can be attributed to the apparent higher degree of clustering in these cells. The RS cells have a larger spread in pixel intensities than H cells, as evidenced by their increased c.o.v. This means that the DNA density in these multinucleated cells is more varied than for the mononucleated H cells.

These structures might appear due to changes in the condensation of the DNA. As H and RS cells are larger, the DNA might also be spread out over a larger volume. If the spreading is uneven, this could lead to local "patches" of DNA. It might also be linked to a difference in chromatin organization, possibly measured with chromosome conformation capture techniques [Nagano et al., 2013], between these cells and healthy lymphocytes. The DNA-free space in these cells has been measured. An increase in the DNA-free space in HL compared to lymphocytes, as well as the formation of "holes" in the nucleus, has been observed.

To check whether the DNA-free space or the holes represented nucleoli, UBF was stained. During HL progression from H cells to RS cells with increased multinuclearity, it was found that both the portion of DNA-free space filled with UBF and the rate of visible holes filled with UBF decreased significantly. Nucleoli can be disrupted in cancer [Boulon et al., 2010], which would explain why the UBF signal is not confined to one nucleolus per subnucleus in the malignant cells.

Other superresolution methods, or microscopes that perform optical sectioning, could lead to similar images as in FIGS. 1 and 4. Such images should then lead to similar granulometry results. The structures with frequency content that is within the pass-band of the objective lens might be recovered from laser widefield microscopy images using post-processing methods.

The measurements herein quantitatively revealed the progressive disruption of nuclear DNA organization in Hodgkin's lymphoma. A progressive trend in the organization of DNA using superresolution microscopy has been shown. This trend starts at the control lymphocytes, moves towards Hodgkin cells, and then progresses to Reed-Sternberg cells. The same trend with increasing multinuclearity has been found within the population of Reed-Sternberg cells.

The study on an HL cell line has been performed. An embedding medium with proper refractive index can be used. It may be possible to do this in tissue 2D slices, in particular lymph node biopsies.

The measured features of the nuclear architecture follow a progressive trend with progressive cell conditions in HL. More aggressive cases of HL can, in some cases, be identified based on the telomere organization of the H and RS cells in those tumors [Knecht et al., 2012]. The nuclear DNA structure might, therefore, also be related to the aggressiveness of HL. Whether the measurements presented here are correlated with clinical outcome, could be investigated by comparing HL cases of patients who respond to treatment versus those who recur.

The changes in the DNA organization were studied. It has been shown a difference for both the DNA structure and DNA-free space in the nucleus. Both nuclear and nucleolar remodeling has been found.

Example 2

Plasma cell disorders are a spectrum of diseases characterized by the proliferation of neoplastic plasma cells of B-cell lineage that produce monoclonal immunoglobulin [Rajkumar et al., 2006; Dimopoulos and Terpos, 2010]. This spectrum includes asymptomatic conditions such as monoclonal gammopathy of unknown significance (MGUS) as well as the symptomatic malignant condition, multiple myeloma (MM) [Rajkumar et al., 2006; Dimopoulos and Terpos, 2010]. The risk of progression from MGUS to symptomatic MM is approximately 1% per year [Rajkumar, 2005; Korde et al., 2011].

Abnormal plasma cells in MGUS and MM are thought to be morphologically identical [Kastritis and Dimopoulos, 2014]. These cells also share common cytogenetic features as well as genetic and epigenetic alterations [Klewes et al., 2013; Kastritis and Dimopoulos, 2014]. Although MGUS and MM cells can be distinguished from normal plasma cells by genetic and phenotypic markers, there is no single marker that distinguishes between MGUS and MM cells [Zingone and Kuehl, 2011].

The mammalian cell nucleus has a unique structural and functional organization [Raska et al., 1992; Cooper, 2000]. It contains morphologically distinct chromatin domains and protein subcompartments that fit into a limited space [Qumsiyeh, 1999; Cremer and Cremer, 2001]. Several studies have shown that a specific nuclear architecture is related to transcriptional activity [van Driel and Verschure, 2001; Rajapakse and Groudine, 2011]. A better understanding of nuclear structure of the myeloma cell might reveal underlying molecular mechanisms in the pathogenesis of the disease.

Conventional light microscopy, with a resolution limited by the diffraction limit of the objective lens, has been widely used in modern cell and cancer biology. The recent development of superresolution fluorescence microscopy techniques allows us to evaluate spatial relationships within subcellular and suborganelle structures beyond the diffraction limit [Hell, 2007; Heilemann, 2010; Schermelleh et al., 2010; Leung and Chou, 2011]. Such optical nanoscopy techniques provide the ability of accurate measurements of subcellular structures at a level previously achieved only by electron microscopy [Baddeley et al., 2010].

Three-dimensional structured illumination microscopy (3D-SIM) is a super-resolution method, which provides a higher image resolution than conventional widefield microscopy [Gustafsson, 2008; Schermelleh et al., 2010]. In short, a periodic illumination pattern results in heterodyne detection of high frequency information that would otherwise be lost. Images are acquired for multiple pattern orientations and phases and computationally recombined as a superresolution image [Gustafsson et al., 2008; Shroff et al., 2009; Wicker et al., 2013]. 3D-SIM has revealed the subcellular localization of key proteins in cells [Sonnen et al., 2012; Strauss et al., 2012], the fine details of nuclear envelope [Schermelleh et al., 2008], chromosome structure [Carlton, 2008; Flors and Earnshaw, 2011; Green et al., 2011], or even the specialized cellular structure such as endothelial cell fenestrations [Cogger et al., 2010] and the cytokinetic Z ring in live bacteria [Turnbull et al., 2014]. The application of this technique is compatible with both fixed and live cells [Hirvonen et al., 2009]. Using 3D-SIM, as shown in Example 1 and Righolt et al. (2014) the DNA organization in the interphase nuclei of Hodgkin's lymphoma and revealed a significant increase in submicron DNA structures of Hodgkin cells and Reed-Sternberg cells compared to normal lymphocytes that clearly distinguish the three cell types from each other.

In this study, 3D-SIM has been used to examine the three-dimensional ultrastructure of the interphase nucleus of myeloma cells from untreated MM patients and compared them to malignant plasma cells of untreated MGUS patients and normal lymphocytes of both patient groups.

Materials and Methods

Patients

The study population in this Example consisted of a total of 20 patients, which where subdivided into two groups: MM (N=10) and MGUS (N=10). All patients conformed to the diagnostic criteria according to the International Myeloma Working Group (IMWG) [Kyle and Rajkumar, 2009]. All blood samples were collected before the start of any treatment. All patients were treatment naive. Control lymphocytes were examined from the identical patients (i.e., from patients presenting with MM or MGUS).

Isolation of Lymphocytes and Myeloma Cells

Ten milliliters peripheral blood from each patient was collected in EDTA-treated tubes. Mononuclear cells were overlaid in Ficoll-Paque (GE Healthcare Life Sciences, Baie d'Urfe, Quebec, Canada) and separated by centrifugation at 200 g for 30 min. The removed buffy coat was washed with 10 ml of a 1× phosphate buffered saline (PBS) solution.

DAPI Staining

The isolated cells were subsequently placed onto slides. The slides were incubated in 3.7% formaldehyde (Sigma-Aldrich, Oakville, Ontario, Canada) for 30 min and washed three times in 1×PBS for 5 min each while shaking at room temperature. Slides were stained with 4',6-diamidino-2-phenylindole (DAPI) (0.1 μl/ml) and incubated in the dark for 3 min. Excess DAPI was removed with ddH2O. The slides were then mounted with Vestashield (Vector Laboratories, Burlington, Ontario, Canada). The slides were covered with a coverslip (No. 1½, Schott, Mainz, Germany) and sealed with nail polish. The slides were stored at 4° C. until imaging.

Identification of Myeloma Cells

In this study, myeloma and lymphocyte nuclei have been identified based on size and intensity of the DAPI staining.

Image Acquisition

All images from isolated cells were captured using a Zeiss Elyra PS1 SIM equipped with a Zeiss Plan Apochromat inverted 63×/1.40 oil immersion objective lens using an Andor EM-CCD iXon 885 camera and a 1.6× tube lens at room temperature. The DAPI channel was obtained with 405 nm laser excitation, 23 μm diffraction grating and filter cube SR Cube 07. The lateral pixel size, $\Delta x$ and $\Delta y$, was 79 nm in the recorded images and 40 nm in the reconstructed image. The z-stacks were acquired by capturing slices taken at 91 nm intervals through each nucleus, and consisted of 60-85 slices collected sequentially. Cell nuclei were chosen by the operator. A field of view was selected and the z-stack boundaries were defined manually.

The 3D-SIM and widefield images were reconstructed using ZEN 2012 black edition (Carl Zeiss, Jena, Germany). Image stacks were exported as 16-bit tiff image sequences.

The image processing was performed in Matlab (MathWorks, Natick, Mass.) with the toolbox DIP image [Luengo Hendriks et al., 1999]. A central z-plane was manually selected. The nucleus was automatically detected by isodata thresholding. The granulometry of the DNA structure was measured with a morphological sieve applied to the error-function clipped images [Duin et al., 2007; Luengo Hendriks et al., 2007]. The coefficient of variation and the skewness of the intensity histogram over the detected region were also calculated. See Example 1 for full details of the methodology.

Statistical Analysis

Group data were expressed as mean±SD. For 3D-SIM imaging data, the distributions were compared using two-sided, two-sample Kolmogorov-Smirnov (KS) tests to determine the significance of difference. P-values of <0.05 were considered statistically significant.

Results

Clinical characteristics of all patients included in this study are described in Table 1. The two patient groups were similar in age. The average age of the MM and MGUS groups is 67.4±14.7 and 67.2±14.9 years, respectively. The MM group was composed of 3 cases at stage I, 5 cases at stage II and 2 cases at stage III according to the International Staging System (ISS) [Greipp et al., 2005]. The majority of the patients in both groups were classified in the IgG group. The percentage of bone marrow plasma cells (BMPC) and the level of secreted monoclonal protein (M-protein) increased with disease progression to symptomatic MM (Table 1).

TABLE 1

Clinical characteristics of patients

| Clinical characteristic | MGUS patients | MM patients |
|---|---|---|
| Mean age (year) | 67.2 ± 14.9 | 67.4 ± 14.7 |
| Bone marrow plasma cells (BMPC, %) | 4.2 ± 2.5 | 38.8 ± 33.5 |
| Immunoglobulin isotype (mg/dL) | | |
| IgG | 16.1 ± 8.6 | 34.5 ± 25.9 |
| IgA | 3.9 ± 2.8 | 2.6 ± 5.3 |
| IgM | 2.3 ± 4.4 | 0.4 ± 0.2 |
| M protein (g/L) | 9.2 ± 7.2 | 29.1 ± 18.8 |

Lymphocytes and myeloma nuclei from MM and MGUS samples were identified and then imaged using 3D-SIM. After acquisition and image reconstruction (see Materials and Methods section of this Example), the intranuclear DNA structure was determined. A total of 534 lymphocytes, 259 MGUS and 279 MM nuclei have been analysed. FIG. 10 illustrates the nuclear DNA structure of normal lymphocyte as well as MGUS and MM nuclei. Nuclear DNA structures were well defined and clearly visible in 3D-SIM images compared to widefield images. In normal lymphocytes, the DNA structure within the nucleus generally appeared as a fine-grained texture and exhibited uniform distribution. On the contrary, myeloma cells had a relatively coarse texture and uneven distribution of their nuclear DNA.

Additionally, numerous well-defined areas void of DAPI staining ("holes") in 3D-SIM images of the myeloma nuclei have been observed. The areas void of "holes" were difficult to observe in the corresponding widefield images (FIG. 10). While most of the myeloma nuclei have the large scale "holes" within their nuclei, these structures were hardly detected in lymphocyte nuclei.

To quantify whether there are differences between normal lymphocytes and myeloma nuclei, granulometry was used to evaluate the size distribution of the DNA structure and the DNA-free space (see Example 1). Granulometry analysis shows that there are differences at both the submicron and micron sizes. The differences at the micron level correspond to differences in the nuclear size, whereas the differences in the nuclear organization of DNA occur at submicron size. Normal lymphocytes have the smallest amount of submicron DNA structure.

The two-sided, two-sample Kolmogorov-Smirnov (KS) test showed that the amount of the intranuclear submicron DNA structure in myeloma nuclei was significantly increased compared to normal lymphocyte nuclei ($P=10^{-88}$). The KS test also showed significant alterations in the granule size distribution of the DNA-free space of myeloma nuclei compared to lymphocyte nuclei ($P=10^{-168}$ for MM nuclei vs lymphocytes and $P=10^{-231}$ for MGUS nuclei vs lymphocytes), as described in Table 2.

Among myeloma nuclei, the DNA-free space of MM nuclei and MGUS nuclei was significantly different ($P=10^{-8}$) as measured by dark granulometry and shown in FIG. 11. However, there was no significant difference of the DNA submicron structure between MM and MGUS nuclei ($P=0.68$) when light granulometry was measured. There was no difference of nuclear DNA structure and DNA-free space of normal lymphocyte nuclei in MM and MGUS patients ($P=0.99$). Note that all samples examined were from treatment naïve patients (see Materials and Methods section of this Example).

TABLE 2

The differences of intranuclear organization between MM, MGUS and lymphocyte nuclei using the two-sided, two-sample Kolmogorov-Smirnov (KS) tests

| Differences in intranuclear organization | P value |
|---|---|
| DNA submicron structure | |
| Lymphocyte vs MGUS nuclei | $2.0 \times 10^{-88}$ |
| Lymphocyte vs MM nuclei | $2.5 \times 10^{-88}$ |
| MGUS vs MM nuclei | 0.68 |
| Intranuclear DNA-free space | |
| Lymphocyte vs MGUS nuclei | $4.1 \times 10^{-231}$ |
| Lymphocyte vs MM nuclei | $1.1 \times 10^{-168}$ |
| MGUS vs MM nuclei | $1.0 \times 10^{-8}$ |

In summary, the application of 3D-SIM microscopy revealed details of nuclear DNA organization in MM and MGUS nuclei. The data showed that myeloma nuclei have significantly increased submicron DNA structure and an increase in DNA-free space compared to normal lymphocyte nuclei. Moreover, MGUS and MM nuclei differ significantly in their dark granulometries ("empty nuclear space") indicating that MGUS and MM represent two distinct types of plasma cell malignancies. The differences between MGUS and MM nuclei have been herein visualized and quantified at the organizational DNA level.

Discussion

Chromosomes and other nuclear components are non randomly organized within the nucleus [Kumaran et al., 2008; Cremer and Cremer, 2010]. Each chromatin territory influences gene expression and nuclear function [Sproul et al., 2005; Kumaran et al., 2008; Solovei et al., 2009]. In the present study, the 3D-SIM has been used to provide a quantitative evaluation of the size distribution of nuclear DNA in abnormal myeloma nuclei at a level of accuracy beyond the conventional optical diffraction limit of light microscopes. 3D-SIM allows increased resolution in all three directions, allowing the study of the nuclear architecture at ultrastructure level. This study showed a significant change of the size distribution of nuclear DNA of MM nuclei compared to MGUS and normal lymphocytes. This alteration reflects the structural changes of the cell nucleus and the distribution of nuclear DNA.

3D-SIM yields information of the alterations of DNA organization that may reflect genetic changes in interphase nucleus.

It has been observed herein that MGUS nuclei have significantly higher DNA-free space than MM nuclei, whereas no difference in nuclear DNA submicron structure was measured between the two types of nuclei compared to normal lymphocytes. The difference in DNA-free space between MGUS and MM nuclei might be resulting from changes in the condensation and the rearrangement of the DNA. These alterations are likely associated with changes in DNA organization as revealed by 3D-SIM.

The study herein demonstrates differences in the nuclear DNA organization between MGUS and MM nuclei. The characteristic morphological changes between malignant and premalignant cells are not visible by conventional light microscopy due to mostly nanoscale changes, for example, nuclear chromatin texture [Liu et al., 2014]. The findings herein provide information to differentiate myeloma nuclei between MGUS and MM patients. The data herein also show that 3D-SIM can visualize morphological changes enabling the identification of premalignant cells.

The study herein showed significantly altered nuclear DNA organization of MM nuclei compared to MGUS and normal lymphocyte nuclei.

Example 3

In Western countries around 20% of HL patients relapse after their initial treatment. For this reason a prognostic test could help stratify patient in appropriate risk groups which could tailor the way the disease is treated. Recent studies identified differences between patients that had good responses to treatment and patients with refractory or relapsing HL. These differences were seen in their telomere architecture [Knecht et al., 2012], their gene expression profiles [Steidl et al., 2012] and Epstein-Barr virus levels in the case of EBV-associated HL [Kanakry et al., 2013]. Genomic instability in general is associated with refractory/relapsing HL. In EBV-associated cases the EBV encoded LMP1 oncoprotein is targeting the shelterin complex [Knecht et al., 2013].

In this study, lymph node biopsies from ten patients were analyzed in a blinded fashion.

Materials & Methods

Patients

For this study, 10 Hodgkin's lymphoma patient diagnostic lymph node biopsy samples were examined in a blinded manner. The samples were derived from diagnostic lymph node biopsies of treatment naïve patients. After completion of the experimental study, the clinical information was unblinded and the patient information obtained. There were seven patients who responded to the current treatment regimen and three patients who relapsed (see Table 3).

Serial 5 micron sections of paraffin-embedded diagnostic lymph nodes were obtained. CD30 staining confirmed the presence of Hodgkin and Reed-Sternberg cells. Paraffin was removed by three cycles of xylene, and the slides were slowly rehydrated with decreasing series of ethanol. Prior to DAPI (0.1 µg/ml) staining of the tissue, the same slides had underwent a telomere hybridization protocol using a Cy3- labeled PNA probe (DAKO) for another analysis [Adebayo Awe et al., 2013]. This shows for example that biopsy slides even if previously stained, can be used in the methods described herein.

Imaging of DAPI-stained nuclei was performed with a Zeiss Elyra PS1 SIM microscope. This microscope setup included a Plan-Apochromat 63×/1.40 Oil immersion objective, and Andor EM-CCD iXon 885 camera and a 1.6× tube lens. Images of the DAPI-stained samples were acquired using 405 nm laser excitation, a 23 µm diffraction grating and a SR Cube 07 filter cube. Lateral pixel sizes were 79 nm for the recorded images and 40 nm for the reconstructed images. The axial steps size between z-planes was 91 nm. Image reconstruction was done with ZEN 2012 black edition using standard settings with two exceptions. Clipping was turned off and the regularization parameter was manually set to $10^{-3}$.

A visual observer manually selected rectangular regions of interest around specific cells and selected a central z-plane for further processing. Image analysis was performed as described previously above in Example 1. The segmentation method was, however, slightly adjusted as follows.

The DNA structure and the structure of DNA-free space was then measured using granulometry [Luengo Hendriks et al., 2007]. All computations were implemented using the DIPimage toolbox for Matlab [Luengo Hendriks et al., 1999].

Segmentation Method

The segmentation method to automatically detect the cells outlines was based on the method described in Example 1 with the following changes.

Let $D_{orig}(x)$ be the input DAPI image of the cell after SIM reconstruction. Now a blurred version is defined as $$D_{smooth}(x) = G_\sigma(x) \otimes D_{orig}(x), \quad (2)$$

where $G_\sigma(x) \otimes$ indicates convolution with a Gaussian function. The width $\sigma=100$ nm was used for these cells. A histogram of the image $D_{smooth}(x)$ was calculated with 256 bins. The intensity level $i_{bg}$ was taken as the intensity with the largest histogram bin and seen as the background. Now several binary images (or masks) were calculated. An estimate of the background is given by $$M_{low}(x) = \begin{cases} 1 & \text{if } D_{smooth}(x) < 0.95 i_{bg} \\ 0 & \text{elsewhere} \end{cases} \quad (3)$$

Note that some of the DNA-free space within the cell would have intensity values below $0.95 i_{bg}$ as well. The second mask, $M_{high}(x)$, is defined by thresholding the unsharp masked image $D_{orig}(x) - 0.9 D_{smooth}(x)$ with the isodata algorithm [Ridler and Calvard, 1978], removing the edge objects and selecting the largest connected component after binary closing with a round structure element (SE) with a 200 nm radius and filling all holes. A temporary mask, $M_{diff}(x)$, is now binary true where $M_{high}(x)$ is true and $M_{low}(x)$ is false. Several morphological operations are successively performed on $M_{diff}(x)$ to get the final mask for the cell, $M_{cell}(x)$. First, a binary opening was applied with a circular SE of radius 100 nm. Second, all connected objects touching the edge of the image were removed. Third, a binary closing with a circular SE of radius 100 nm was performed. Fourth, all remaining holes were filled in. An finally, the largest connected object image was taken as $M_{cell}(x)$, the mask for the cell.

Results

The DNA structure and the structure of the DNA-free space were analyzed for three types of cells (lymphocytes, H cells and RS cells) on 10 diagnostic patient lymph node biopsies. The experiments were performed blinded to the clinical information of the patients. Afterwards the patients were grouped based on their clinical outcome: a non-relapsed group of seven patients and a relapsed group of three patients. See Table 3 for a summary of clinical information about these patients.

This study used superresolution microscopy to examine primary pre-treatment Hodgkin's lymphoma samples. These images were successfully recorded in 3D for at least 30 DAPI-stained nuclei within each HL sample. Because the samples were 5 µm tissue sections, cells could be cut partway through. For this reason only 2D central (x,y)-slices were used for further analysis. Relevant slices for a representative example figure of all three cell types are depicted in FIG. 12. Some structural differences between the cell types are clearly visible in these images. In particular, the malignant cells show an increase in smaller structure size of both the DNA structure and the structure of the DNA-free space.

The slices were analyzed using granulometry as described in Materials and methods section of this Example. Granulometry on the image itself yielded the size distribution of the DNA structure; granulometry on the negative of the image yielded the size distribution of the structure of the DNA-free space. The granulometries for the cells of one type within one sample were initially combined to 30 groups (10 patients×3 cell types).

The lymphocytes can act as an internal control because these healthy cells, were found to generally not differ in relapsed and non-relapsed pre-treatment patients. There are 45 distinct pairs that can be formed to compare between two patients out of the 10 patient cohort. The two-sided, two-sample Kolmogorov-Smirnov test led to an average p-value of 0.844 for the DNA structure of control lymphocytes, none of the p-values in these comparisons were significant at either the 5% or 10% significant levels. A similar analysis for the structure of the DNA-free space of control lymphocytes led to an average p-value of 0.847, and one p=0.048, which was the only significant difference at both the 5% and 10% significance levels. Because 1 in 90 is 1.1%, which is both lower than 5% and 10%, it can be concluded that the lymphocytes are comparable and that the analysis method is valid and can be used.

Next the results were analyzed in 6 groups for both the DNA structure and the structure of the DNA-free space. The results were grouped by cell type (lymphocytes, H cells and RS cells) and clinical outcome (non-relapsed and relapsed). The resulting distributions of structure sizes are plotted in FIG. 13. All distributions were compared with two-sample, two-sided Kolmogorov-Smirnov tests. It is clear that the lymphocyte structure is very different from the malignant cell structure of H and RS cells combined for both the DNA and the DNA-free space. There were a total of 16 such comparisons; their p-values ranged from $10^{-43}$ to $10^{-9}$.

The lymphocytes were indistinguishable between non-relapsed and relapsed patients (p=0.999994 for the DNA structure and p=1 for the structure of the DNA-free space). The H cells of the Hodgkin's patients were also the same between non-relapsed and relapsed patients; the DNA structure led to p=0.9995 and the structure of the DNA-free space led to p=0.9987. The narrative changed, however, for RS cells. While the DNA-free space had a structure that was not significantly different between non-relapsed and relapsed patients (p=0.60), the DNA structure was, however, significantly different at the 5% level between RS cells of non-relapsed and relapsed patients, p=0.012. The RS cells of relapsed patients have a larger relative amount of submicron DNA structure.

These data suggest that RS cells of patients entering long lasting remission and of relapse patients differ significantly. These findings imply that aggressive forms of HL already contain subtle DNA changes identifiable in their RS cells at the time of the primary diagnosis. These changes suggest a different disease course related to additional mechanisms of tumorigenesis in the relapse group of patients.

Discussion

This study was undertaken to investigate in primary pre-treatment Hodgkin's lymphoma patient tissues whether superresolution microscopy could reveal distinct DNA structure(s) specific for mono-nucleated Hodgkin cells and multinucleated Reed-Sternberg cells. The advantage of using diagnostic lymph nodes lies in the possibility of using each patient's lymphocytes as internal controls for the analysis of nuclear architecture of DNA. It provides a unique experimental set up in which the same cell lineage can be compared in its normal and malignant form. For example, one can compare HL cells with lymphocytes within one patient to see changes.

The lymphocytes showed the same structure for all patients, which served both as an internal control to show that DNA structure of normal cells and indicated similar measurement results for the methods discussed in this paper. In contrast, the DNA structure is significantly different between RS cells of non-relapsed and relapsed patients, whereas the DNA structure of their H cells is the same. This shows that the HL aggressiveness could be predicted from the RS cells and their nuclear architecture.

Around 20% of patients relapse in current HL treatment modalities. If the particular aggressiveness of a patient's HL could be predicted a priori, before the start of treatment, then it might be possible to treat (tailored therapy) and follow-up patients differently depending on the nature of their HL. Such an approach might further increase the success rate of HL treatment.

Different cancers differ in how genomic instability plays a role. The changes to the DNA structure and the structure of the DNA-free space may be different for different cancers, if existent at all. Changes in this structure have, been observed in multiple myeloma as described in Example 2 and [Sathitruangsak et al., 2015].

TABLE 3

Diagnostic lymph node biopsies of 10 HL patients (prior to treatment) were examined in this study. The clinical information of these patients is summarized below. (The term "ABVD" refers herein to Adriamycin, Bleomycin, Vinblastine and Dacarbazine and the term "MOPP" refers herein to Mustargen, Oncovin, Procarbazine and Prednisone.)

| Sex | Age | Stage | Treatment | Outcome (after end of treatment) |
| --- | --- | --- | --- | --- |
| M | 28 | IIIB, bulky | 6x MOPP/ABVD | Remission for 111 months |
| M | 18 | IIA | 3x ABVD | Remission for 76 month |
| F | 43 | IA | Radiation only | Remission for 86 months |
| M | 38 | IIA | 4x ABVD | Remission for 80 months |
| M | 25 | IIB | 8x ABVD | Remission for 62 months |
| F | 51 | IIIB | 8x ABVD | Relapsed at 4 months |
| F | 20 | IIA | 3x ABVD | Remission for 52 months |
| F | 56 | IVB | 8x ABVD | Relapsed at 11 months |

TABLE 3-continued

Diagnostic lymph node biopsies of 10 HL patients (prior to treatment) were examined in this study. The clinical information of these patients is summarized below. (The term "ABVD" refers herein to Adriamycin, Bleomycin, Vinblastine and Dacarbazine and the term "MOPP" refers herein to Mustargen, Oncovin, Procarbazine and Prednisone.)

| Sex | Age | Stage | Treatment | Outcome (after end of treatment) |
| --- | --- | --- | --- | --- |
| F | 30 | IIIA | 6x ABVD | Relapsed at 41 months |
| F | 22 | IIB | 4x ABVD | Remission for 38 months |

Example 4

This Example uses conventional microscopy (widefield microscopy) and an image sharpening method for images analysis by granulometry.

As shown in Example 3, the DNA structure is different for RS cells in patients that are prone to relapse. This structural difference is, not the only change, the nuclear architecture changes in various ways. There may be other ways to measure the DNA structure than granulometry on SIM images. Contrast enhancement by unsharp masking [Young et al., 1998] on conventional microscope images may, for example, reveal relevant structure as well.

As shown herein, DAPI, and other minor DNA groove binding dyes, may be employed to study DNA structure and the structure of DNA free space in tumor cells.

In Examples 1 to 3, images were obtained using a SIM technique. The SIM technique permits obtaining SIM images which show details that may be further used for granulometry analysis.

Conventional microscopy, such as widefield microscopy, may also be used for the granulometry analysis. For example, an image obtained using widefield microscopy may be processed further to obtain a second image that may show approximately the same amount of detail as a SIM image. Such image processing may be performed using image sharpening or contrast enhancement techniques.

Unsharp masking is one of a wide variety of image sharpening or contrast enhancement techniques that could be used.

FIG. 14 shows exemplary images of the cells. The top row of FIG. 14 (Ai, Bi, Ci), shows light granulometry input images (co-called "DNA structures" or so-called "positive images"). The bottom row of FIG. 14, shows dark granulometry input images (co-called "structures of DNA-free space" or co-called "negative images"). Images Ai and Aii were obtained using SIM, images Bi and Bii were obtained using widefield microscopy and unsharp masking. Images Ci and Cii (right column of FIG. 14) represent the differences between SIM images and widefield and unsharp masking (Bi and Bii) images.

The unsharp masking may be implemented by subtracting a blurred version of an original image from the original image. In this case the blurring was performed by convolving the image with a Gaussian with a standard deviation of 3 pixels (120 nm). Other blurring settings or algorithms would/could produce a similar result.

The unsharp masking may lead to an approximately equally detailed input image for the granulometry. It has been determined that the SIM images (Ai and Aii) and the widefield unsharp masking images (Bi and Bii) look visually the same and show similar details. Moreover, the difference images (Ci and Cii) show no structure. That is, the small differences are rounding differences and have no bearing on the structure measurements. Although the images may not be identical; they show the same structure.

The input images for the granulometry being similar, or approximately the same, the results of granulometry would be similar as well. Based on the above, it is expected that widefield images may be used to measure DNA structure and the structure of the DNA-free space as well.

Example 5

This Example describes classification of the granulometry results based on the CDF values. It should be noted that although the CDF values were calculated here for submicron DNA structure, the same classification may be applicable to CDF values obtained for DNA low space (.e.g. using dark images). It should be also noted that similar results may be obtained using other probability and statistics characteristics instead of CDF values. For example, one or more values of probability density function(s) may be calculated and used in the method described herein.

Table 4 shows values calculated for several study cases (patients) for an exemplary DNA structure (RS cells) diameter of 500 nm. It should be noted that any size (or a combination of sizes) for a DNA structure or a DNA low space below 1000 nm may be used. Table 4 also indicates whether each of the cases studied relapsed or remission.

It is clear from Table 4 that the relapsed cases have higher value of CDF than the CDF value for the cases in remission. Therefore, CDF values for one or more diameters of the DNA structure may be used to classify the cells. For example, CDF values at a certain diameter may be compared to each other in order to determine whether the case will result in remission or relapse.

Similar CDF values may be determined for other structures and diameters. For example, CDF may be determined for DNA structures and/or structures of DNA-free space. For example, CDF may be determined for H cells and/or RS cells at any length scale (e.g. any diameter of the structure element in the granulometry).

After the values of CDF have been determined, standard classification techniques may be used. Standard classification techniques may include, for example, not limited to, Fisher discriminant analysis, Bayesian classifiers, and neural networks.

For example, a cut-off value of CDF may be selected based on a described specificity and/or sensitivity. Knowing the cut-off value, it may be possible to predict whether the patients would likely relapse or would stay in remission. Treatment decisions can include assessing the likelihood of relapse.

The same technique of determining whether the patients would likely relapse or would stay in remission may be used with images obtained using a conventional technique. For example, processed widefield images obtained using widefield microscopy and then processed as described, for example, in Example 4.

TABLE 4

Status of studied cases and values of CDF for the 500 nm diameter of a DNA structure in Reed-Sternberg cells (RS cells). CDF values were obtained by linear interpolation of CDF values obtained from the granulometry.

| Case number | CDF value | Status |
| --- | --- | --- |
| Case 263 | 0.305479 | Remission |
| Case 101 | 0.312668 | Remission |
| Case 006 | 0.326659 | Remission |
| Case 054 | 0.335048 | Remission |
| Case 066 | 0.348729 | Remission |
| Case 208 | 0.350576 | Relapse |
| Case 123 | 0.353369 | Remission |
| Case 162 | 0.354065 | Relapse |
| Case 190 | 0.373074 | Remission |
| Case 217 | 0.382786 | Relapse |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Adebayo Awe J, Xu M C, Wechsler J, Benali-Furet N, Cayre Y E, Saranchuk J, Drachenberg D, Mai S. 2013. Three-Dimensional Telomeric Analysis of Isolated Circulating Tumor Cells (CTCs) Defines CTC Subpopulations. Transl Oncol 6:51-65.
2. Baddeley D, Chagin V O, Schermelleh L. 2010. Measurement of replication structures at the nanometer scale using super-resolution light microscopy. Nucl Acids Res 38(2):1-11.
3. Bins M, Landeweerd G H, Gelsema E S, van Montfort L H, Halie M R. 1981. Texture of white blood cells expressed by the counting densitogram. Cytometry 1:321-324.
4. Boulon S, Westman B J, Hutten S, Boisvert F M, Lamond A I. 2010. The nucleolus under stress. Mol Cell 40:216-27.
5. Boveri T. 1914. Zur Frage der Entstehung maligner Tumoren. Jena: Fischer.
6. Boveri T. 2008. Concerning the Origin of Malignant Tumours by Theodor Boveri. Translated and annotated by Henry Harris. Journal of Cell Science 121:1-84.
7. Branco M R, Pombo A. 2006. Intermingling of chromosome territories in interphase suggests role in translocations and transcription-dependent associations. PLoS Biol 4:e138.
8. Brousset P, al Saati T, Chaouche N, Zenou R C, Schleifer D, Chittal S, Delsol G. 1997. Telomerase activity in reactive and neoplastic lymphoid tissues: infrequent detection of activity in Hodgkin's disease. Blood 89:26-31.

9. Carlton P M. 2008. Three-dimensional structured illumination microscopy and its application to chromosome structure. Chromosome Res 16(3):351-365.
10. Cogger V C, McNerney G P, Nyunt T, DeLeve L D, McCourt P, Smedsrod B, Le Couteur D G, Huser T R. 2010. Three-dimensional structured illumination microscopy of liver sinusoidal endothelial cell fenestrations. J Struct Biol 171 (3):382-388.
11. Cooper G M. 2000. The cell: A molecular approach. 2nd edition. Sunderland (Mass.): *Sinauer Associates Internal organization of the nucleus.*
12. Cragg G E, So P T. 2000. Lateral resolution enhancement with standing evanescent waves. Opt Lett 25:46-8.
13. Cremer T, Cremer C. 2001. Chromosome territories, nuclear architecture and gene regulation in mammalian cells. Nature Rev Genet 2:292-301.
14. Cremer T, Cremer C. 2006a. Rise, fall and resurrection of chromosome territories: a historical perspective. Part I. The rise of chromosome territories. Eur J Histochem 50:161-76.
15. Cremer T, Cremer C. 2006b. Rise, fall and resurrection of chromosome territories: a historical perspective. Part II. Fall and resurrection of chromosome territories during the 1950s to 1980s. Part Ill. Chromosome territories and the functional nuclear architecture: experiments and models from the 1990s to the present. Eur J Histochem 50:223-72.
16. Cremer T, Cremer C. 2010. Chromosome territories. Cold Spring Harb Perspect Biol 2(3):1-22.
17. Dimopoulos M A, Terpos E. 2010. Multiple myeloma. Ann Oncol 21(7):vii143-vii 150.
18. Drexler H G, Gaedicke G, Lok M S, Diehl V, Minowada J. 1986. Hodgkin's disease derived cell lines HDLM-2 and L-428: comparison of morphology, immunological and isoenzyme profiles. Leuk Res 10:487-500.
19. Drexler H G, Gignac S M, Hoffbrand A V, Minowada J. 1989. Formation of multinucleated cells in a Hodgkin's-disease-derived cell line. Int J Cancer 43:1083-90.
20. Duin R P W, Juszczak P, Paclik P, Pekalska E, de Ridder D, Tax D M J, Verzakov S. 2007. *PRTools, A Matlab toolbox for pattern recognition. Delft, The Netherlands: Delft University of Technology.*
21. Einstein A J, Wu H-S, Sanchez M, Gil J. 1998. Fractal characterization of chromatin appearance for diagnosis in breast cytology. The Journal of Pathology 185:366-381.
22. Flors C, Earnshaw W C. 2011. Super-resolution fluorescence microscopy as a tool to study the nanoscale organization of chromosomes. Curr Opin Chem Biol 15(6):838-844.
23. Fong K W, Li Y, Wang W, Ma W, Li K, Qi R Z, Liu D, Songyang Z, Chen J. 2013. Whole-genome screening identifies proteins localized to distinct nuclear bodies. J Cell Biol 203:149-64.
24. Frohn J T, Knapp H F, Stemmer A. 2000. True optical resolution beyond the Rayleigh limit achieved by standing wave illumination. Proc Natl Acad Sci USA 97:7232-6.
25. Green L C, Kalitsis P, Chang T M, Cipetic M, Kim J H, Marshall O, Turnbull L, Whitchurch C B, Vagnarelli P, Samejima K, Earnshaw W C, Choo K H A, Hudson D F. 2011. Contrasting roles of condensin I and condensin II in mitotic chromosome formation. J Cell Sci 125(6):1591-1604.
26. Greipp P R, Miguel J S, Dude B G M, Crowley J J, Barlogie B, Blade J, Boccadoro M, Child J A, Avet-Loiseau H, Kyle R A, Lahuerta J J, Ludwig H, Morgan G, Powles R, Shimizu K, Shustik C, Sonneveld P, Tosi P, Turesson I, Westin J. 2005. International staging system for multiple myeloma. J Clin Oncol 23:3412-3420.
27. Gu M. 2000. Advanced Optical Imaging Theory. Berlin: Springer.
28. Guffei A, Sarkar R, Klewes L, Righolt C, Knecht H, Mai S. 2010. Dynamic chromosomal rearrangements in Hodgkin's lymphoma are due to ongoing three-dimensional nuclear remodeling and breakage-bridge-fusion cycles. Haematologica 95:2038-46.
29. Gustafsson M G. 2000. Surpassing the lateral resolution limit by a factor of two using structured illumination microscopy. J Microsc 198:82-7.
30. Gustafsson M G, Shao L, Carlton P M, Wang C J, Golubovskaya I N, Cande W Z, Agard D A, Sedat J W. 2008. Three-Dimensional Resolution Doubling in Wide-Field Fluorescence Microscopy by Structured Illumination. Biophys J 94(12):4957-4970.
31. Hannen E J M, Van Der Laak J A W M, Manni J J, Pahlplatz M M M, Freihofer H P M, Slootweg P J, Koole R, De Wilde P C M. 1998. An image analysis study on nuclear morphology in metastasized and non-metastasized squamous cell carcinomas of the tongue. The Journal of Pathology 185:175-183.
32. Heilemann M. 2010. Fluorescence microscopy beyond the diffraction limit. J Biotechnol 149(4):243-251.
33. Hein N, Hannan K M, George A J, Sanij E, Hannan R D. 2013. The nucleolus: an emerging target for cancer therapy. Trends Mol Med 19:643-54.
34. Heine B, Hummel M, Demel G, Stein H. 1999. Hodgkin and Reed-Sternberg cells of classical Hodgkin's disease overexpress the telomerase RNA template (hTR). J Pathol 188:139-45.
35. Heintzmann R, Cremer C G. 1999. Laterally modulated excitation microscopy: improvement of resolution by using a diffraction gratingeditor^editors, p 185-196.
36. Hell S W. 2007. Far-field optical nanoscopy. Science 316:1153-1158.
37. Hirvonen L M, Wicker K, Mandula O, Heintzmann R. 2009. Structured illumination microscopy of a living cell. Eur Biophys J 38:807-812.
38. Hsu S M, Zhao X, Chakraborty S, Liu Y F, Whang-Peng J, Lok M S, Fukuhara S. 1988. Reed-Sternberg cells in Hodgkin's cell lines HDLM, L-428, and KM-H2 are not actively replicating: lack of bromodeoxyuridine uptake by multinuclear cells in culture. Blood 71:1382-9.
39. Johnson N A, Savage K J, Ludkovski O, Ben-Neriah S, Woods R, Steidl C, Dyer M J, Siebert R, Kuruvilla J, Klasa R, Connors J M, Gascoyne R D, Horsman D E. 2009. Lymphomas with concurrent BCL2 and MYC translocations: the critical factors associated with survival. Blood 114:2273-9.
40. Jones R J, Gocke C D, Kasamon Y L, Miller C B, Perkins B, Barber J P, Vale M S, Gerber J M, Gellert L L, Siedner M, Lemas M V, Brennan S, Ambinder R F, Matsui W. 2009. Circulating clonotypic B cells in classic Hodgkin lymphoma. Blood 113:5920-6.
41. Kanakry J A, Li H, Gellert L L, Lemas M V, Hsieh W S, Hong F, Tan K L, Gascoyne R D, Gordon L I, Fisher R I, Bartlett N L, Stiff P, Cheson B D, Advani R, Miller T P, Kahl B S, Horning S J, Ambinder R F. 2013. Plasma Epstein-Barr virus DNA predicts outcome in advanced Hodgkin lymphoma: correlative analysis from a large North American cooperative group trial. Blood 121:3547-53.
42. Kastritis E, Dimopoulos M A. 2014. Monoclonal gammopathy of undetermined significance (MGUS) and smoldering multiple myeloma. In: Schey S A Yong K L Marcus R Anderson K C editors. Myeloma: Pathology, diagnosis and treatment. New York: Cambridge University Press. p 121-133.
43. Kim P J. 1969. On the Exact and Approximate Sampling Distribution of the Two Sample Kolmogorov-Smirnov Criterion D mn, m≤n. Journal of the American Statistical Association 64:1625-1637.
44. Klewes L, Vallente R, Dupas E, Brand C, Grun D, Guffei A, Sathitruangsak C, Awe J A, Kuzyk A, Lichtensztejn D, Tammur P, Ilus T, Tamm A, Punab M, Rubinger M, Olujohungbe A, Mai S. 2013. Three-dimensional nuclear telomere organization in multiple myeloma. Transl Oncol 6:749-756.
45. Knecht H, Bruderlein S, Wegener S, Lichtensztejn D, Lichtensztejn Z, Lemieux B, Moller P, Mai S. 2010. 3D nuclear organization of telomeres in the Hodgkin cell lines U-HO1 and U-HO1-PTPN1: PTPN1 expression prevents the formation of very short telomeres including "t-stumps". BMC Cell Biol 11:99.
46. Knecht H, Johnson N, Haliotis T, Lichtensztejn D, Mai S. 2015. Combined 3D Immuno-FISH Analysis of Primary Hodgkin (H) and Reed-Sternberg (RS) Cells Reveals Disruption of Telomere-TRF2 Interaction and Identifies Hodgkin's Lymphoma Shelterin Associated Dideaseeditor^editors. 20th EHA Congress. Vienna.
47. Knecht H, Kongruttanachok N, Sawan B, Brossard J, Prevost S, Turcotte E, Lichtensztejn Z, Lichtensztejn D, Mai S. 2012. Three-dimensional Telomere Signatures of Hodgkin- and Reed-Sternberg Cells at Diagnosis Identify Patients with Poor Response to Conventional Chemotherapy. Transl Oncol 5:269-77.
48. Knecht H, Righolt C, Mai S. 2013. Genomic Instability: The Driving Force behind Refractory/Relapsing Hodgkin's Lymphoma. Cancers (Basel) 5:714-25.
49. Knecht H, Sawan B, Lichtensztejn D, Lemieux B, Wellinger R J, Mai S. 2009. The 3D nuclear organization of telomeres marks the transition from Hodgkin to Reed-Sternberg cells. Leukemia 23:565-73.
50. Korde N, Kristinsson S Y, Landgren O. 2011. Monoclonal gammopathy of undetermined significance (MGUS) and smoldering multiple myeloma (SMM): novel biological insights and development of early treatment strategies. Blood 17 (21):5573-5581.
51. Kumaran R I, Thakar R, Spector D L. 2008. Chromatin dynamics and gene positioning. Cell 132(6):929-934.
52. Kuppers R. 2009. The biology of Hodgkin's lymphoma. Nat Rev Cancer 9:15-27.
53. Kuppers R, Engert A, Hansmann M L. 2012. Hodgkin lymphoma. J Clin Invest 122:3439-47.
54. Kyle R A, Rajkumar S V. 2009. Criteria for diagnosis, staging, risk stratification and response assessment of multiple myeloma. Leukemia 23(1):3-9.
55. Lajoie V, Lemieux B, Sawan B, Lichtensztejn D, Lichtensztejn Z, Wellinger R, Mai S, Knecht H. 2015. LMP1 mediates multinuclearity through downregulation of shelterin proteins and formation of telomeric aggregates. Blood 125:2101-10.
56. Leung B O, Chou K C. 2011. Review of super-resolution fluorescence microscopy for biology. Appl Spectrosc 65(9):967-980.
57. Liu Y, Uttam S, Alexandrov S, Bista R K. 2014. Investigation of nanoscale structural alterations of cell nucleus as an early sign of cancer. BMC Biophys 7(1):1-16.
58. Lobo I. 2008. Chromosome abnormalities and cancer cytogenetics. Nature Education 1(1):35-43.
59. Luengo Hendriks C L, Rieger B, van Ginkel M, van Kempen G M P, van Vliet L J. 1999. DlPimage: a scientific image processing toolbox for MATLABeditor^editors: Delft University of Technology.
60. Luengo Hendriks C L, van Kempen G M P, van Vliet L J. 2007. Improving the accuracy of isotropic granulometries. Pattern Recognition Letters 28:865-872.
61. MacLeod R A, Spitzer D, Bar-Am I, Sylvester J E, Kaufmann M, Wernich A, Drexler H G. 2000. Karyotypic dissection of Hodgkin's disease cell lines reveals ectopic subtelomeres and ribosomal DNA at sites of multiple jumping translocations and genomic amplification. Leukemia 14:1803-14.
62. Markaki Y, Smeets D, Fiedler S, Schmid V J, Schermelleh L, Cremer T, Cremer M. 2012. The potential of 3D-FISH and super-resolution structured illumination microscopy for studies of 3D nuclear architecture. BioEssays 34:412-426.
63. Martin-Subero J I, Knippschild U, Harder L, Barth T F, Riemke J, Grohmann S, Gesk S, Hoppner J, Moller P, Parwaresch R M, Siebert R. 2003. Segmental chromosomal aberrations and centrosome amplifications: pathogenetic mechanisms in Hodgkin and Reed-Sternberg cells of classical Hodgkin's lymphoma? Leukemia 17:2214-9.
64. Morgan G J, Walker B A, Davies F E. 2012. The genetic architecture of multiple myeloma. Nat Rev Cancer 12(5):335-348.
65. Nagano T, Lubling Y, Stevens T J, Schoenfelder S, Yaffe E, Dean W, Laue E D, Tanay A, Fraser P. 2013. Single-cell Hi-C reveals cell-to-cell variability in chromosome structure. Nature 502:59-64.
66. Natarajan S, Juneja M, Pallam N K, Boaz K, Mohindra A, Lewis A. 2012. A novel technique to assess chromatin texture using pixel optical densitometry in oral squamous cell carcinoma. Microscopy Research and Technique 75:1119-1123.
67. Newcom S R, Kadin M E, Phillips C. 1988. L-428 Reed-Sternberg cells and mononuclear Hodgkin's cells arise from a single cloned mononuclear cell. Int J Cell Cloning 6:417-31.
68. Norrback K F, Enblad G, Erlanson M, Sundstrom C, Roos G. 1998. Telomerase activity in Hodgkin's disease. Blood 92:567-73.
69. Pienta K J, Partin A W, Coffey D S. 1989. Cancer as a disease of DNA organization and dynamic cell structure. Cancer Res 49:2525-32.
70. Qumsiyeh M B. 1999. Structure and function of the nucleus: Anatomy and physiology of chromatin. Cell Mol Life Sci 55(8-9):1129-1140.
71. Rajapakse I, Groudine M. 2011. On emerging nuclear order. J Cell Biol 192(5):711-721.
72. Rajkumar S V. 2005. MGUS and smoldering multiple myeloma: Update on pathogenesis, natural history, and management. Hematology Am Soc Hemalol Educ Program 1:340-345.
73. Rajkumar S V, Dispenzieri A, Kyle R A. 2006. Monoclonal gammopathy of undetermined significance, Waldenström macroglobulinemia, AL amyloidosis, and related plasma cell disorders: diagnosis and treatment. Mayo Clin Proc 81(5):693-703.
74. Raska I, Dundr M, Koberna K. 1992. Structure-function subcompartments of the mammalian cell nucleus as revealed by the electron microscopic affinity cytochemistry. Cell Biol Int Rep 16(8):771-789.
75. Ridler T W, Calvard S. 1978. Picture Thresholding Using an Iterative Selection Method. Systems, Man and Cybernetics, IEEE Transactions on 8:630-632.

76. Righolt C H, Guffei A, Knecht H, Young I T, Stallinga S, van Vliet L J, Mai S. 2014. Differences in nuclear DNA organization between lymphocytes, Hodgkin and Reed-Sternberg cells revealed by structured illumination microscopy. J Cell Biochem 115:1441-1448.
77. Sathitruangsak C, Righolt C H, Klewes L, Tammur P, Ilus T, Tamm A, Punab M, Olujohungbe A, Mai S. 2015. Quantitative superresolution microscopy reveals differences in nuclear DNA organization of multiple myeloma and monoclonal gammopathy of undetermined significance. J Cell Biochem 116:704-10.
78. Schermelleh L, Carlton P M, Haase S, Shao L, Winoto L, Kner P, Burke B, Cardoso M C, Agard D A, Gustafsson M G, Leonhardt H, Sedat J W. 2008. Subdiffraction multicolor imaging of the nuclear periphery with 3D structured illumination microscopy. Science 320:1332-6.
79. Schermelleh L, Heintzmann R, Leonhardt H. 2010. A guide to super-resolution fluorescence microscopy. J Cell Biol 190(2):165-175.
80. Shroff S A, Fienup J R, Williams D R. 2009. Phase-shift estimation in sinusoidally illuminated images for lateral superresolution. J Opt Soc Am A Opt Image Sci Vis 26(2):413-424.
81. Solovei I, Kreysing M, Lanctôt C, Kösem S, Peichl L, Cremer T, Guck J, Joffe B. 2009. Nuclear architecture of rod photoreceptor cells adapts to vision in mammalian evolution. Cell 137(2):356-368.
82. Sonnen K F, Schermelleh L, Leonhardt H, Nigg E A. 2012. 3D-structured illumination microscopy provides novel insight into architecture of human centrosomes. Biol Open 1(10):965-976.
83. Sproul D, Gilbert N, Bickmore W A. 2005. The role of chromatin structure in regulating the expression of clustered genes. Nat Rev Genet 6:775-781.
84. Steidl C, Diepstra A, Lee T, Chan F C, Farinha P, Tan K, Telenius A, Barclay L, Shah S P, Connors J M, van den Berg A, Gascoyne R D. 2012. Gene expression profiling of microdissected Hodgkin Reed-Sternberg cells correlates with treatment outcome in classical Hodgkin lymphoma. Blood 120:3530-40.
85. Strauss M P, Liew A T F, Turnbull L, Whitchurch C B, Monahan L G, Harry E J. 2012. 3D-SIM super resolution microscopy reveals a bead-like arrangement for FtsZ and the division machinery: Implications for triggering cytokinesis. PLoS Biol 10(9):1-17.
86. Szczurek A T, Prakash K, Lee H K, Zurek-Biesiada D J, Best G, Hagmann M, Dobrucki J W, Cremer C, Birk U. 2014. Single molecule localization microscopy of the distribution of chromatin using Hoechst and DAPI fluorescent probes. Nucleus 5:331-40.
87. Tanabe H, Muller S, Neusser M, von Hase J, Calcagno E, Cremer M, Solovei I, Cremer C, Cremer T. 2002. Evolutionary conservation of chromosome territory arrangements in cell nuclei from higher primates. Proc Natl Acad Sci USA 99:4424-9.
88. Turnbull L, Strauss M P, Liew A T, Monahan L G, Whitchurch C B, Harry E J. 2014. Super-resolution imaging of the cytokinetic Z ring in live bacteria using fast 3D-structured illumination microscopy (f3D-SIM). J Vis Exp 29(91):1-13.
89. van Driel R, Verschure P J. 2001. Nuclear organization and gene expression: Visualization of transcription and higher order chromatin structure. In: Mapping protein/DNA interactions by cross-linking [Internet]. Paris: Institut national de la sant& #233; et de la recherche m& #233;dicale.
90. Verbeek P W, van Vliet L J. 1993. Estimators of 2D edge length and position, 3D surface area and position in sampled grey-valued images. Bioimaging 1:47-61.
91. Vergani L, Fugazza G, Chessa L, Nicolini C. 1999. Changes of chromatin condensation in one patient with ataxia telangiectasia disorder: A structural study. Journal of Cellular Biochemistry 75:578-586.
92. Wang Y, Maharana S, Wang M D, Shivashankar G V. 2014. Super-resolution microscopy reveals decondensed chromatin structure at transcription sites. Sci Rep 4:4477.
93. Wicker K, Mandula O, Best G, Fiolka R, Heintzmann R. 2013. Phase optimisation for structured illumination microscopy. Opt Express 21(2):2032-2049.
94. Young I T. 1977. Proof without prejudice: use of the Kolmogorov-Smirnov test for the analysis of histograms from flow systems and other sources. J Histochem Cytochem 25:935-41.
95. Young I T, Gerbrands J J, Van Vliet L J. 1998. Image Processing Fundamentals. In Madisetti V K, Williams D B, editor^editors. The Digital Signal Processing Handbook. Boca Raton, Fla.: CRC Press in cooperation with IEEE Press, p 51.51-51.81.
96. Young I T, Verbeek P W, Mayall B H. 1986. Characterization of chromatin distribution in cell nuclei. Cytometry 7:467-474.
97. Zingone A, Kuehl W M. 2011. Pathogenesis of monoclonal gammopathy of undetermined significance (MGUS) and progression to multiple myeloma. Semin Hematol 48(1):4-12.

The invention claimed is:

1. A method of measuring a characteristic of nuclear organization of DNA of a cancer test cell sample, comprising:
   a. characterizing nuclear organization of DNA of the test cell sample comprising:
      i. obtaining DNA image data of the cancer test cell sample nuclei using superresolution microscopy, using a microscope that performs optical sectioning, or wide-field microscopy;
      ii. processing the image data using granulometry to obtain one or more data points corresponding to DNA occupied space and DNA low space; and
   b. quantifying a feature of the DNA occupied space and a feature of the DNA low space, the quantifying providing the characteristic of nuclear organization of DNA.

2. The method of claim 1, further comprising comparing the quantified features to a control selected from another cancer sample, a control sample or a threshold; and identifying an increase or decrease in the quantified feature compared to the control;
   the increase or decrease in the quantified feature compared to the control providing the characteristic of nuclear organization of DNA of the cancer test sample.

3. The method of claim 2, wherein the control sample is an internal control.

4. The method of claim 1, wherein the feature quantified is selected from one or more of 1) the size distribution of length scales of the DNA occupied space 2) the size distribution of length scales of the DNA low space; 3) the density distribution of the DNA occupied space; 4) the density distribution of the DNA low space; 5) the density of the DNA occupied space and 6) the density of the DNA low space.

5. The method of claim 4, wherein the DNA occupied space comprises submicron DNA structures or micron DNA structures.

6. The method of claim 5, wherein an increase in the number of submicron DNA structures or a change in the number of micron DNA structures of approximately 1 micrometer to approximately 3 µm is indicative of a poor clinical characteristic.

7. The method of claim 6, wherein an increase in the number of the number of DNA structures that are about 200 to about 700 nm is indicative of a poor clinical characteristic.

8. The method of claim 1, wherein the image data is obtained from a 2D object or a 3D object.

9. The method of claim 1, wherein the test cancer cell comprises interphase nuclei.

10. The method of claim 1, wherein obtaining the image data comprises a combination of an optical microscopy technique and image reconstruction algorithms.

11. The method of claim 10, wherein obtaining the image data comprises acquisitioning z-stack data and reconstructing the 3D-SIM images.

12. The method of claim 11, wherein the 3D-SIM images are reconstructed with a regularization parameter set to 10-3 and clipping turned off.

13. The method of claim 1, wherein the processing and quantifying comprise selecting a central z-plane, and measuring the granulometry of the DNA occupied space and the DNA low space using a morphological sieve applied to the image data.

14. The method of claim 1, wherein quantifying comprises determining an intensity histogram for skewness and coefficient of variation, wherein a difference in the skewness compared to the control is indicative of a poor clinical characteristic.

15. The method of claim 1, wherein the cancer test sample comprises 1) one or more of mononucleated Hodgkin (H) cells and multinucleated Reed Sternberg (RS) cells or 2) one or more of monoclonal gammopathy of unknown significance (MGUS) and multiple myeloma (MM) cells.

16. The method of claim 1, wherein the cancer test cell sample is a tissue section, a blood sample or a lymph node aspirate.

17. The method of claim 1, wherein a decrease or increase in the size of DNA low space compared to a normal cell is indicative of a Hodgkin's disease.

18. The method of claim 17, wherein the difference between the distribution between Hodgkin's test cell and control is detected at a length scale of about 0.6 µm to about 2 µm.

19. The method of claim 1, wherein the method further comprises measuring a nucleoli constituent.

20. The method of claim 19, wherein the nucleoli constituent is upstream binding factor (UBF) or another protein present in nucleoli or nuclear bodies.

21. The method of claim 19, wherein a change in DNA low space negative for a nucleoli constituent is indicative of a poor clinical feature.

22. The method of claim 1, wherein the method is for identifying the number of one or more of H and RS cells, for one or more of 1) providing a diagnosis, 2) for monitoring progression, disease transition, treatment efficacy, treatment efficacy after surgery, radiation or other treatment, 3) for assessing cancer heterogeneity and 4) for clinical trial group assignment.

23. The method of claim 22, wherein the RS cells are differentially nucleated RS cells.

24. The method of claim 1, further comprising determining if the cancer test cell sample, obtained from a patient, comprises RS cells with submicron DNA structure being above or below a selected threshold.

25. The method of claim 24, further comprising:
a. if the CDF is below the threshold, determining that the patient will be more likely in remission; and
b. if the CDF is above the threshold, determining that the patient will be more likely in recession.

26. The method of claim 24, wherein the selected threshold is determined by:
performing the steps of the method for a plurality of cancer test cell samples collected from a group of patients with known remission or recession outcome;
for each of the plurality of cancer test cell samples, calculating values of CDF of their submicron size of DNA occupied space; and
analyzing the values of CDF, using at least one classification technique, to determine the selected threshold.

27. The method of claim 26, wherein the CDF and the selected threshold is determined for a specific size of the submicron structure of DNA occupied space.

28. The method of claim 26, wherein the diameter of the submicron structure of DNA occupied space is 500 nm.

29. The method of claim 28, wherein the selected threshold is determined by:
performing the steps of the method for a plurality of cancer test cell samples collected from a group of patients with known remission or recession outcome;
for each of the plurality of cancer test cell samples, calculating values of CDF of their submicron size of DNA low space; and
analyzing the values of CDF, using at least one classification technique, to determine the selected threshold.

30. The method of claim 29, wherein the CDF and the selected threshold is determined for a specific size of the submicron structure of DNA low space.

31. The method of claim 29, wherein the diameter of the submicron structure of DNA low space is 500 nm.

32. The method of claim 1, wherein cancer test cell sample is a cancer test cell sample obtained from a subject.

33. The method of claim 32, wherein the cancer test cell sample is obtained from a subject with or suspected of having Hodgkin's lymphoma, multiple myeloma or a precursor thereof, prostate cancer, breast cancer or lung cancer.

34. The method of claim 1, wherein the superresolution microscopy is three-dimensional structured illumination microscopy (3D-SIM), airy scan, or photo-activated localization microscopy (PALM).

35. The method of claim 1, further comprising determining if the cancer test cell sample, obtained from a patient, comprises RS cells with cumulative distribution function (CDF) of a submicron structure of DNA occupied space or DNA low space being above or below a selected threshold.

36. The method of claim 1, wherein the method is for identifying the proportion of one or more of H and RS cells, for one or more of 1) providing a diagnosis, 2) for monitoring progression, disease transition, treatment efficacy, treatment efficacy after surgery, radiation or other treatment, 3) for assessing cancer heterogeneity and 4) for clinical trial group assignment.

37. A method for characterizing a cancer test cell sample, the method comprising:
a. obtaining a DNA image data of the cancer test cell sample using superresolution microscopy; and
b. analyzing, on a computer processor, the DNA image data using granulometry to obtain at least one characteristic corresponding to DNA occupied space and at least one characteristic corresponding to DNA low space, the at least one characteristic corresponding to DNA occupied space being 1) a size distribution of the DNA occupied space or 2) a cumulative distribution function (CDF) of DNA occupied space, and the at least one characteristic corresponding to DNA low space being 1) a size distribution of the DNA low space or 2) a CDF of DNA low space.

38. The method of claim 37, wherein analyzing the DNA image data using granulometry further comprises obtaining a negative of the DNA image.

39. A method for determining if a sample comprising Hodgkin's lymphoma (HL) cells obtained from a patient includes Reed Sternberg (RS) cells with a submicron DNA structure above a selected threshold, the method comprising a. measuring intranuclear submicron DNA architecture of multinucleated RS cells in the sample;
  i. obtaining DNA image data of the sample cancer cell nuclei using superresolution microscopy;
  ii. processing the image data using granulometry to obtain one or more data points corresponding to DNA occupied space and DNA low space;
b. quantifying a feature of the DNA occupied space, wherein the feature is submicron DNA structure length, wherein the submicron DNA structure length is a discrete length, one or more discrete lengths or a distribution of lengths, wherein the distribution is compared to at least one threshold;
c. identifying samples with submicron DNA structure above the selected threshold; and
d. treating the patient with a treatment for HL if the patient sample comprises RS cells with a submicron DNA structure above the selected threshold, wherein the selected threshold is associated with relapse.

40. The method of claim 39, wherein the superresolution microscopy is three-dimensional structured illumination microscopy (3D-SIM), airy scan, or photo-activated localization microscopy (PALM).

* * * * *